United States Patent
Holakovsky et al.

(10) Patent No.: US 11,224,705 B2
(45) Date of Patent: Jan. 18, 2022

(54) INHALER

(71) Applicant: Boehringer Ingelheim International GmbH, Ingelheim am Rhein (DE)

(72) Inventors: Holger Holakovsky, Schöneberg (DE); Jens Besseler, Bingen am Rhein (DE); Jessica Frentzel-Beyme, Gau-Algesheim (DE); Frank Herrmann, Duisburg (DE)

(73) Assignee: BOEHRINGER INGELHEIM INTERNATIONAL GMBH, Ingelheim am Rhein (DE)

( * ) Notice: Subject to any disclaimer, the term of this patent is extended or adjusted under 35 U.S.C. 154(b) by 615 days.

(21) Appl. No.: 16/076,879

(22) PCT Filed: Feb. 20, 2017

(86) PCT No.: PCT/EP2017/053728
§ 371 (c)(1),
(2) Date: Aug. 9, 2018

(87) PCT Pub. No.: WO2017/144386
PCT Pub. Date: Aug. 31, 2017

(65) Prior Publication Data
US 2019/0060586 A1    Feb. 28, 2019

(30) Foreign Application Priority Data
Feb. 24, 2016   (EP) .................................... 16020049

(51) Int. Cl.
*A61M 15/00*   (2006.01)
(52) U.S. Cl.
CPC ........ *A61M 15/003* (2014.02); *A61M 15/005* (2014.02); *A61M 15/0026* (2014.02);
(Continued)

(58) Field of Classification Search
CPC ............ A61M 15/003; A61M 15/0041; A61M 15/0026; A61M 15/0035; A61M 15/005;
(Continued)

(56) References Cited

U.S. PATENT DOCUMENTS

| 4,811,731 A | 3/1989 | Newell |
| 4,860,740 A * | 8/1989 | Kirk .................. A61M 15/0028 |
| | | 128/203.15 |

(Continued)

FOREIGN PATENT DOCUMENTS

| CA | 2509521 C | 8/2012 |
| EP | 0147755 A2 | 7/1985 |

(Continued)

OTHER PUBLICATIONS

International Search Report for corresponding application, PCT/EP2017/053728, dated Jun. 16, 2017.

*Primary Examiner* — Colin W Stuart
*Assistant Examiner* — Douglas Y Sul
(74) *Attorney, Agent, or Firm* — Matthew B. Dernier, Esq.

(57) ABSTRACT

An inhaler for inhalation of a formulation in powder form includes: a magazine which is rotatable and contains pre-dosed doses of the formulation in capsules, a housing which is substantially round or disc-shaped, the housing having a housing part in which the rotatable magazine is disposed, where the housing part is fixedly coupled to the rotatable magazine, and is removable from the housing in order to facilitate replacement of the magazine by inserting a new magazine.

16 Claims, 15 Drawing Sheets

(52) U.S. Cl.
CPC .... *A61M 15/0035* (2014.02); *A61M 15/0041* (2014.02); *A61M 2202/0007* (2013.01); *A61M 2202/064* (2013.01); *A61M 2205/6045* (2013.01)

(58) Field of Classification Search
CPC .... A61M 2205/6045; A61M 2201/007; A61M 2201/064; A61J 1/00; A61J 1/03; A61J 1/06; B65D 83/04; B65D 83/0445; B65D 83/0454
USPC .......... 206/528, 533, 538, 539, 534.1, 534.2
See application file for complete search history.

(56) References Cited

U.S. PATENT DOCUMENTS

| | | | |
|---|---|---|---|
| 4,889,114 A | 12/1989 | Kladders | |
| 5,415,162 A * | 5/1995 | Casper | A61M 15/0045 128/203.12 |
| 5,685,294 A | 11/1997 | Gupte et al. | |
| 6,948,492 B2 * | 9/2005 | Wermeling | A61M 11/06 128/200.14 |
| 8,298,575 B2 | 10/2012 | Hochrainer | |
| 8,584,669 B2 | 11/2013 | Besseler et al. | |
| 2002/0170560 A1 | 11/2002 | Young | |
| 2003/0178024 A1 * | 9/2003 | Allan | A61M 15/0015 128/200.24 |
| 2004/0099676 A1 * | 5/2004 | Anderson | A61M 15/008 221/25 |
| 2004/0188546 A1 * | 9/2004 | Tabata | A61M 15/0085 239/436 |
| 2005/0017017 A1 * | 1/2005 | Crosby | A61J 1/03 221/25 |
| 2005/0268909 A1 | 12/2005 | Bonney | |
| 2006/0157053 A1 * | 7/2006 | Barney | A61M 15/0025 128/200.23 |
| 2007/0163580 A1 * | 7/2007 | Braithwaite | A61M 15/0003 128/203.21 |
| 2008/0160076 A1 | 7/2008 | Hochrainer | |
| 2008/0202515 A1 * | 8/2008 | Hodson | A61M 15/0075 128/203.21 |
| 2009/0194105 A1 * | 8/2009 | Besseler | A61M 15/0028 128/203.15 |
| 2013/0072878 A1 * | 3/2013 | Avery | A61J 1/06 604/189 |

FOREIGN PATENT DOCUMENTS

| | | |
|---|---|---|
| EP | 1106196 A2 | 6/2001 |
| EP | 2614848 A1 | 7/2013 |
| JP | S62-41668 A | 2/1987 |
| JP | 2005-533584 A | 11/2005 |
| WO | 9102558 A1 | 3/1991 |
| WO | 9200812 A1 | 1/1992 |
| WO | 0007572 A2 | 2/2000 |
| WO | 2002024268 A1 | 3/2002 |
| WO | 2002036189 A1 | 5/2002 |
| WO | 2004052435 A1 | 6/2004 |
| WO | 2005049121 A1 | 6/2005 |
| WO | 2006071512 A1 | 7/2006 |
| WO | 2007118648 A1 | 10/2007 |
| WO | 2009115200 A1 | 9/2009 |
| WO | 2011039307 A2 | 4/2011 |

* cited by examiner

INHALER

The present invention relates to an inhaler according to the preamble of claim 1 or claim 7 and to a magazine according to the preamble of claim 10.

The present invention relates in particular to an inhaler for discharge or inhalation of a formulation which is preferably in powder form, i.e. a powder inhaler.

The formulation is in particular a therapeutic agent or pharmaceutical preparation. Accordingly, in particular, the formulation contains at least one active substance or consists thereof. Thus the formulation serves in particular for medical treatment or other therapeutic purposes.

In the present invention, the formulation is held in capsules, wherein each capsule contains one dose of the formulation. Thus the formulation is pre-dosed into the capsules. In the present invention, the term "capsule" should be understood primarily to mean primary containers having a solid or an at least substantially rigid, in particular dense, integral, closed and/or continuous shell, which in particular can be manipulated and/or opened separately from one another. Preferably, in a further sense according to the present invention the term "capsule" should also be understood to mean other containers, packages or the like with a dose of the formulation in each case, which in particular can be manipulated and/or opened separately from one another.

EP 0 147 755 A2 discloses an inhaler for the inhalation of pharmaceutical preparations in powder form from elongated capsules. The inhaler has a capsule chamber, into which a capsule can be introduced manually in each case. The capsule is pierced lengthwise and thereby opened by manual actuation of an opening device in the capsule chamber. During inhalation, an air stream flowing through the capsule chamber leads to the capsule being moved to and fro in the capsule chamber, wherein the pharmaceutical preparation in powder form is discharged and dispersed in the air stream. The present invention uses this principle in particular, but it can also be used in other techniques for discharging a formulation.

WO 2005/049121 A1 discloses a powder inhaler having a plurality of capsules. The cylindrical capsules are guided upright one behind the other by a rail or are connected to one another in the manner of a chain.

WO 2007/118648 A1 discloses a powder inhaler, which has in particular a plurality of capsule chambers with capsules held therein, wherein each capsule chamber is in particular used only once. The capsules and capsule chambers can be oriented radially, wherein the outlet openings of the capsule chambers can be covered by a common cover. In this case, the capsules and capsule chambers can also be arranged in two axially offset planes. According to another embodiment, the inhaler can also have only one capsule chamber for holding individual capsules successively to be emptied during inhalation. Furthermore, during pivoting a mouthpiece cover can move the capsules forwards and individually into the capsule chambers.

WO 2011/039307 A2 discloses an inhaler for the inhalation of pharmaceutical preparations in powder form from capsules, the inhaler having a replaceable tube which forms a capsule chamber with an adjoining dispensing channel, wherein a capsule has been previously inserted into the capsule chamber. The replaceable tube has openings for needles for piercing the respective capsule, wherein the openings can be closed automatically by a membrane.

A capsule chamber in the sense of the present invention is preferably an at least substantially rigid or firm and/or elongated container or capsule housing having an in particular elongated or cylindrical chamber, in which the respective capsule is in particular movable to and fro for emptying or can be moved in another manner or can be made to vibrate or to oscillate. The capsule chamber preferably has an inlet and an outlet for air, in particular at the opposing ends or end faces thereof.

The object of the present invention is to provide an inhaler and a magazine which allow simple handling and/or a simple or compact design.

The above object is achieved by an inhaler according to claim 1 or claim 7 or by a magazine according to claim 10. Advantageous developments are the subject matter of the subordinate claims.

According to one aspect of the present invention, the inhaler or the housing thereof preferably has an insertable or replaceable housing part which is coupled undetachably to a rotatable magazine which itself contains capsules having a formulation to be inhaled. This allows a very simple, reliable and/or intuitive insertion or replacement of the magazine.

According to another aspect of the present invention, the magazine can be moved further or rotated further to the next capsule preferably by opening and/or closing of a cover which is associated with a mouthpiece of the inhaler. if required, the drive can also take place indirectly, in that the cover drives or tensions a storage element or spring element which for its part effects the required movement at a suitable time.

Alternatively or in addition, it is also possible that by actuation of an actuating element, such as a knob or the like, the magazine can be moved further or rotated further to the next capsule. For example, an actuation of the actuating element can also only enable the further movement, so that the magazine can be moved further or rotated further, in particular only as far as the next capsule or capsule chamber, by the force or energy of a spring mechanism or other energy accumulator after corresponding enabling. A further aspect of the present invention is that the inhaler preferably has a sealing element which can be applied from the exterior to the capsule chamber for closure of a needle opening during the inhalation. This allows a simple structure and a reliable operation.

According to another aspect of the present invention, the capsule chambers are preferably inserted as prefabricated parts into the magazine. This allows a simple or optimised structure, wherein different materials can be used for example for the capsules on the one hand and for a support of the magazine for holding the capsules on the other hand.

According to another aspect of the present invention, the capsules or capsule chambers are preferably secured on or in the magazine by means of a common annular securing element in such a way that they remain in the capsule chambers or in the magazine, and at the same time openings, in particular outlet openings, are provided so that dispensing of the formulation from the respective capsule after opening of the capsule is still possible. In particular, the securing element is in the form of a wire and/or a clamping ring. This allows a simple structure.

According to a further aspect of the present invention, the capsules are preferably elongated and are oriented with their longitudinal axes obliquely with respect to the plane of the ring or an axis of rotation of the magazine. This allows a simple and/or compact structure and/or a simple or intuitive handling, since it makes possible a curvature of the inhaler on a flat face and/or an inclined arrangement of operating elements, such as a piercing device, which is pleasant for a user.

The aforementioned aspects as well as the aspects of the present invention disclosed by the following description can be registered independently of one another, but also in any combination.

Individual aspects, features, characteristics and advantages of the present invention emerge from the claims and the following description of preferred embodiments with reference to the drawings. In the drawings:

Figure 1:
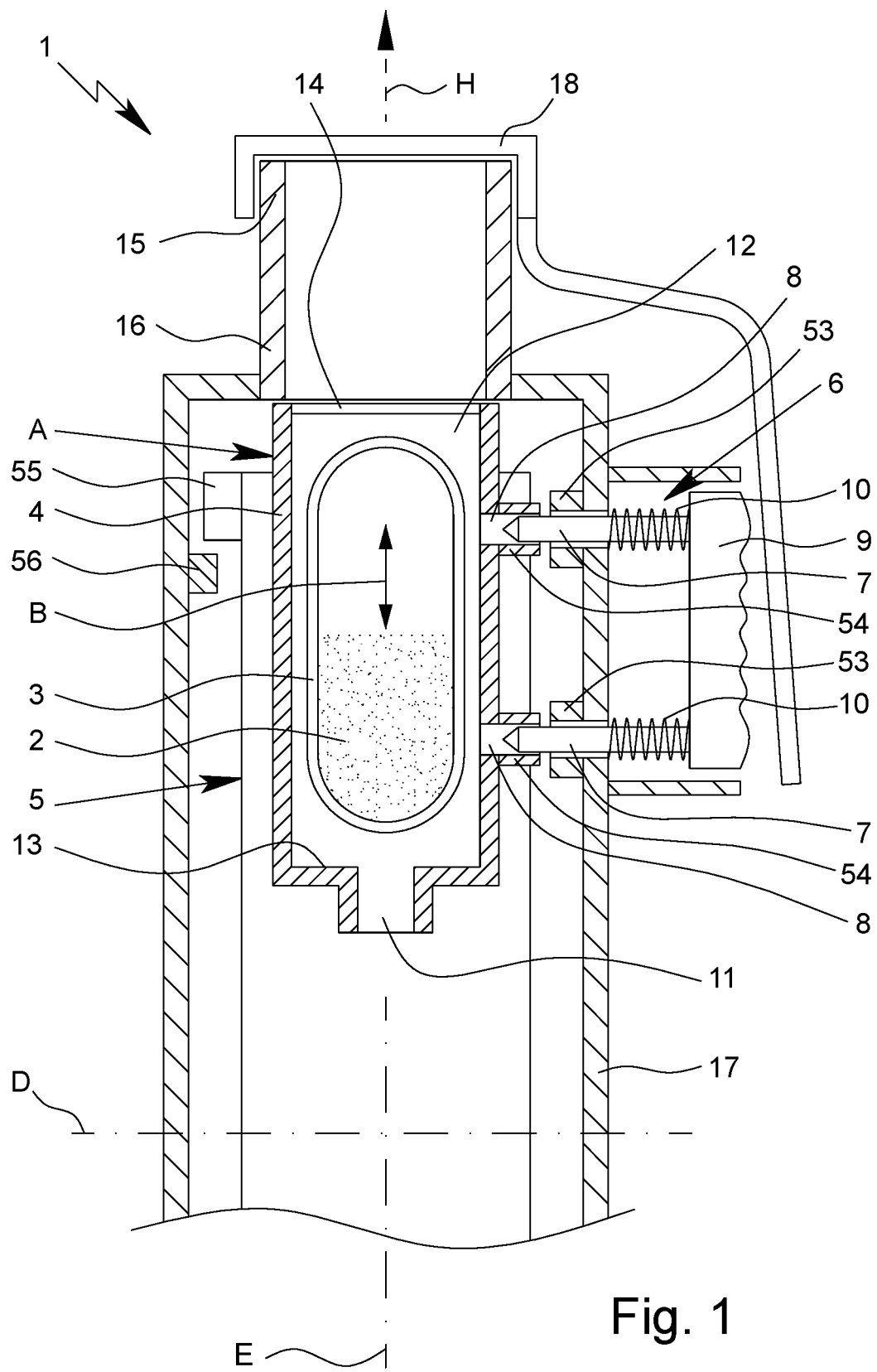
FIG. 1 is a schematic sectional representation of a proposed inhaler for illustration of the functional principle.

In the drawings, the same reference signs are used for the same or similar parts, even if a repeated description is omitted. In particular, the same or corresponding advantages and characteristics also emerge. Individual drawings also may not be true to scale for reasons of representation or simplification.

FIG. 1 shows in a schematic section the basic structure or the basic functional principle of a proposed inhaler 1. The statements in this connection apply in particular correspondingly and additionally to all the embodiments described later.

The inhaler 1 is preferably designed to be portable and in particular only operates mechanically.

The inhaler 1 serves for discharge or atomisation, in particular for inhalation of the formulation 2 preferably in powder form from capsules 3. Thus the formulation 2 is pre-dosed in doses which are received in the capsules 3. If required, the capsules 3 can also contain different formulations 2.

The formulation 2 is in particular a formulation in the sense mentioned at the outset.

The capsules 3 are in particular capsules in the sense mentioned at the outset.

In the schematic section, a capsule 3 is shown inside a capsule chamber 4 of the inhaler 1. The capsule 3 is still closed, i.e. not yet opened.

The capsule chamber 4 is in particular a capsule chamber in the sense mentioned at the outset.

The capsules 3 are preferably elongated. However, in principle the capsules 3 can have any other suitable shape and can be spherical for example.

In principle, the capsules 3 can be produced from or consist of any suitable material. Gelatine is preferably used as capsule material. In this case, gelatine can be used in a mixture with other additions selected from the group consisting of polyethylene glycol (PEG), preferably PEG 3350, glycerol, sorbitol, propylene glycol, PEO-PPO block copolymers and other polyalcohols and polyethers. Particularly preferably, gelatine is used in the mixture with PEG, preferably PEG 3350. A gelatine capsule 3 particularly preferably contains PEG in a proportion of 1 to 10% (wt. %), preferably 3 to 8%. Particularly preferred gelatine capsules 3 contain PEG in a proportion of 4 to 6%, wherein a PEG proportion of approximately 5% is most preferred. In the case of gelatine-containing capsule materials, the capsules 3 preferably have a Tews or halogen dryer moisture content of less than 12%, particularly preferably of ≤10%.

If cellulose derivatives are used as capsule material, the use of hydropropylmethyl cellulose, hydroxypropyl cellulose, methyl cellulose, hydroxymethyl cellulose and hydroxyethyl cellulose is preferred. In this case, hydropropylmethyl cellulose (HPMC) is particularly preferred, particularly preferably HPMC 2910, as capsule material. In the case where cellulose derivatives are used as capsule materials, the degree of Tews or halogen dryer moisture content is preferably less than 8%, particularly preferably less than 5%. Most preferably, before filling with a tiotropium-containing inhalation powder, inhalation capsules 3 made of cellulose derivatives are dried to a Tews or halogen dryer moisture content of less than 4%, particularly preferably less than 2%.

The capsules 3 can each consist of a capsule body and a capsule cap, as disclosed in particular in WO 00/07572 A2. Therefore reference is hereby made explicitly to the content of WO 00/07572 A2 in its entirety. In this two-part construction, plastics material is used in particular as the capsule material. In particular, the capsule body and the capsule cap consist of the same material. They are connected to one another so that a stable, closed cavity of defined volume is formed. In this case plastics material, in particular polyethylene, is particularly preferably used. The capsules 3 can have latching elements which connect the capsule cap firmly to the capsule body.

The capsules 3 and optionally the capsule chambers 4 (if a plurality of capsule chambers 4 are present) are preferably held in a magazine 5 of the inhaler 1. In the schematic section according to FIG. 1, the magazine 5 is only indicated schematically.

The magazine 5 is in particular flat, disc-like or annular. In particular, it has a central or main plane E.

The magazine 5 can preferably be inserted and/or replaced in the inhaler 1.

The capsules 3 and optionally the capsule chambers 4 are arranged or received in or on the magazine 5 preferably at least substantially in an annular manner, preferably with an at least substantially radial orientation.

The magazine 5 is preferably movable or rotatable in the inhaler 1, in this case about an axis of rotation D which is preferably perpendicular to the plane E, in particular so that the magazine 5 can be moved or conveyed or (further) rotated from one capsule 3 to the next capsule 3, particularly preferably in order to bring the capsules 3 individually into a discharge position A, as shown by way of example in FIG. 1.

As already mentioned, each capsule 3 preferably contains one dose of the formulation 2. Since the magazine 5 contains a plurality of capsules 3 and a corresponding number of doses, the inhaler 1 can ensure that a user or patient is supplied with the formulation 2, i.e. a medicament or the like, for example for a week or several weeks or even for a month.

The capsules 3 can preferably be opened individually in the inhaler 1. For opening, the inhaler 1 has an opening device 6 which is associated with the capsule chamber 4 or the capsule 3 or the discharge position A. If required, a plurality of opening devices 3 can be provided which are in each case associated with a capsule chamber 4 or capsule 3. Preferably, however, only one common opening device 6 is provided.

The opening of the capsule 3 preferably takes place in each case by piercing. For this purpose, the opening device 6 preferably has at least one piercing element, such as a needle 7, and in the example shown two needles 7.

The inhaler 1 or the housing 17 thereof can optionally have a needle guide 53, as indicated in FIG. 1. Alternatively or in addition, the capsule chamber 4 can also have needle guides 54. The guides 53, 54 can in particular be tubular or stub-shaped in order to guide the piercing elements or needles 7 in longitudinal movement. However, other structural solutions are also possible.

The capsule chamber 4 preferably has corresponding piercing openings, in this case needle openings 8, for the piercing elements or needles 7. The piercing elements are preferably moved forwards into the piercing openings and close them. The opening device 6 preferably assumes this position after the opening of a capsule 3 during the inhalation, in order to seal the piercing openings at least to a large extent. However, other types of closure or sealing are also possible, in particular from the interior and/or from the exterior or through autonomously or automatically closing piercing openings or closure devices. For sealing or for closure, for example self-sealing membranes or additional sealing elements or the like can be used.

A lateral opening or piercing of the respective capsule 3 preferably takes place. For this purpose, the preferably elongated capsule 3 can be pierced, and thereby opened, longitudinally or laterally and/or transversely with respect to the main flow direction or longitudinal axis of the capsule chamber 4.

Particularly preferably, the capsule 3 is pierced during opening in the region of its two ends and/or laterally.

The piercing or opening of capsules 3 preferably takes place as described in EP 0 147 455 A2, and in this connection reference is hereby made to the content thereof in its entirety.

The opening device 6 preferably has an actuating element 9 which in particular can be actuated manually. The respective capsule 3 can be pierced preferably by actuation or pressing down or pressing in of the actuating element 9.

In the example shown, the piercing elements or needles 7 are preferably firmly connected to the actuating element 9. However, other design solutions are also possible.

The opening device 6 or the actuating element 9 can preferably be actuated against the force of a restoring element, such as at least a spring 10. By means of the restoring element or the spring 10, after the actuation or release of the actuating element 9 the piercing elements or needles 7 preferably resume their retracted starting position, as indicated in FIG. 1. However, other structural solutions are also possible.

The inhaler 1 shown here has a plurality of capsule chambers 4, in each of which a capsule 3 is received and which in each case can in particular be used only once. However, many described functions can be applied to inhalers with only one capsule chamber 4, in which the capsules 3 are successively received for the discharge or emptying. In this case, the capsule chamber 4 is then used multiple times.

The capsule chamber 4 is formed in one or more parts as required. For this purpose, the capsule chamber 4 can also be made up of or produced from different materials and/or by two-component injection moulding.

The capsule chamber 4 preferably has an inlet 11 and an outlet 12 which, in particular axially or on an end face, adjoin an in particular elongated or cylindrical or central movement region or receiving region of the capsule chamber 4 for the capsule 3.

Particularly preferably, the inlet 11 is reduced in diameter relative to the receiving region for the capsule 3, so that preferably an annular shoulder 13 or the like is formed, which forms a stop or a travel limiter for the capsule 3.

The outlet 12 preferably has a securing element 14 associated therewith, which is formed for example in the manner of a grid and/or prevents a movement of the capsule 3 out of the receiving region or out of the capsule chamber 4.

Depending upon the requirements and the design, the securing element 14 can be associated with the magazine 5 or the capsule chamber 4 and/or arranged thereon, but if required can also be formed or retained by the inhaler 1 or a mouthpiece 15 or connecting portion 16.

The geometric conditions preferably correspond at least substantially to the details in EP 0 147 755 A2, which in this connection is hereby introduced as a supplementary disclosure.

During the inhalation or discharge, air or other gas flows through the inlet 11 into the capsule chamber 4, through this or through the receiving region thereof and out of the preferably opposing outlet 12. This stream of air or gas can be produced by breathing in during inhalation and/or by a pressure generator associated with the inhaler 1, such as an air pump, a compressed gas reservoir or the like.

This air stream through the capsule chamber 4 has the effect, in particular due to the Bernoulli effect, that the capsule 3 in the capsule chamber 4 vibrates or oscillates or moves in particular axially to and fro, as indicated by the arrow B in FIG. 1. This movement or vibration B causes or assists the discharge of the formulation 2 from the opened or pierced capsule 3 into the air stream—in particular in the form of very fine particles—and a dispersal of the formulation 2 into the air stream, with which the formulation 2 is finally discharged via the outlet 12 and particularly preferably an adjoining mouthpiece 15 of the inhaler 1, to a user or patient (not shown).

The main discharge direction H of the dispersed formulation 2 by means of the air stream or of the inhaler 1 is indicated in FIG. 1 by a corresponding arrow. Naturally, the discharge is only possible with the cover 18 open and after opening of the respective capsule 3.

The discharge or dispersion of the formulation 2 takes place in particular as described in EP 0 147 755 A2, which in this connection is hereby introduced as a supplementary disclosure. However, in principle the formulation 2 can also be discharged from the capsule 3 in any other suitable manner, for example by rotation of the capsule 3 transversely with respect to the longitudinal axis thereof or the like.

Thus the inhaler 1 preferably has a mouthpiece 15 or some other device for discharging the formulation 2 dispersed in the stream of air or gas.

In the example shown, the mouthpiece 15, in particular a connecting portion 16 thereof, adjoins the capsule chamber 4 or the outlet 12.

The inhaler 1 preferably has a housing 17. This is in particular an external housing.

The mouthpiece 15 is preferably formed or arranged on the housing 17, in particular in a stationary or undetachable manner. However, other design solutions are also possible.

The inhaler 1 or the housing 17 is preferably formed at least substantially in a disc-shaped and/or flat manner.

The mouthpiece 15 is preferably arranged peripherally on the inhaler 1 or housing 17.

The mouthpiece 15 or the main discharge direction 4 of the inhaler 1 preferably extends at least substantially radially or obliquely relative to the axis of rotation D of the magazine 5.

The inhaler 1 preferably has a cover 18 associated with the mouthpiece 15 for selective opening and closing of the mouthpiece 15. With the cover 18 opened the mouthpiece 15 is freed for inhalation. With the cover 18 closed, as shown in FIG. 1, the mouthpiece 15 is preferably covered. Thus inhalation is not possible. In the closed position, the cover 18 can optionally, as indicated in FIG. 1, also cover or in some way lock the opening device 7 or the actuating element 9 thereof, in order to rule out or prevent an (undesirable) opening of the capsule 3 in this state by a user.

The cover 18 is preferably retained or mounted pivotably or rotatably (about a pivot axis coaxially with the axis of rotation D or parallel thereto, for example located externally on the housing 17) on the inhaler 1 or housing 17. Alternatively or in addition, the cover 18 is preferably also movable linearly or radially.

After the emptying of a capsule 3 or after the inhalation of the formulation 2 from a capsule 3, the next capsule 3 is brought or moved into the starting position A. This takes place in particular by further movement or rotation of the magazine 5.

If only one capsule chamber 4 is provided for a plurality of or all of the capsules 3, the emptied capsule 3 is first of all moved out of the capsule chamber 4, for example by opening of the capsule chamber 4 on the inlet side. Subsequently, the next capsule 3 can be moved or introduced into the capsule chamber 4 and the capsule chamber 4 can be closed again. This new capsule 3 is then opened or pierced in particular only just before the next inhalation.

On the other hand, there is no need for opening and closing of the capsule chamber 4 if each capsule 3 is received in a separate capsule chamber 4, i.e. it is only necessary for the capsule chambers 4 to be brought or moved together with the capsules 3 in each case individually into the discharge position A.

For use, a user or patient (not shown) opens the inhaler 1 or the cover 18. In this way, the mouthpiece 15 is freed. Then the opening device 6 is actuated, i.e. the capsule 3 located in the discharge position A is pierced.

The discharge position A designates in particular a position of the capsule 3 adjacent to the mouthpiece 15 or the connecting portion 16 thereof.

In the discharge position A, the capsule 3 or the capsule chamber 4 thereof is located in particular in an extension of the connecting portion 16 or mouthpiece 15 and/or with the longitudinal axis thereof aligned with and/or in an extension of the main discharge direction H and/or in the radial direction, in particular relative to the axis of rotation D of the magazine 5.

Inhalation can take place after the opening or piercing of the capsule 3. Subsequently, the inhaler 1 is closed again. The subsequent capsule 3 is then moved further into the discharge position A, in particular by further movement or further rotation of the magazine 5 to the next capsule 3.

Various embodiments of the proposed inhaler 1 and magazine 5 are explained in greater detail below, wherein the preceding statements and explanations in particular apply correspondingly or additionally, even if repeated description is omitted.

Figure 2:
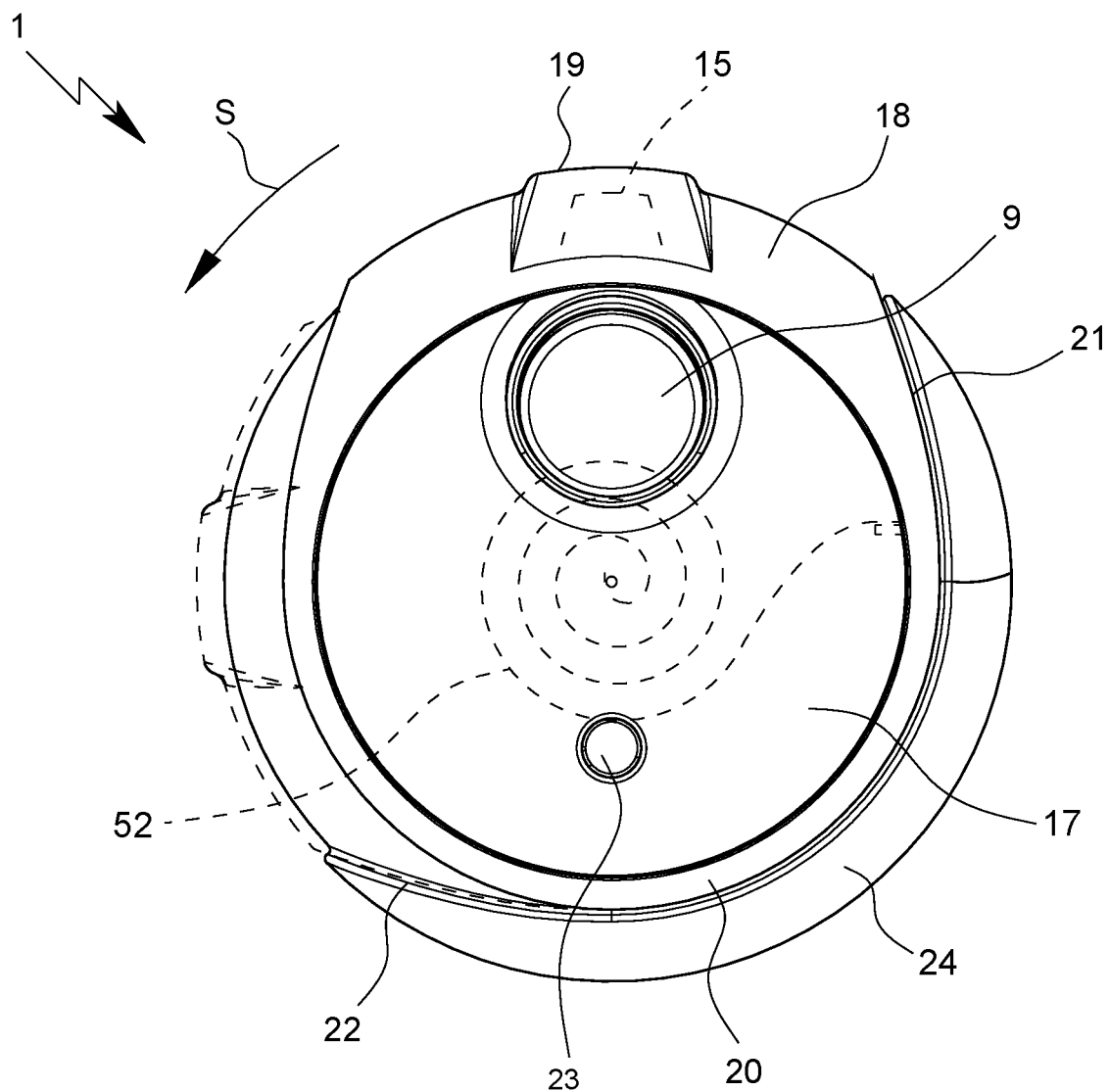
FIG. 2 is a plan view of an inhaler according to a first proposed embodiment.

FIG. 2 shows in a plan view a first embodiment of the proposed inhaler 1 with the cover 18 closed. The opened position of the cover 18 is indicated by broken lines.

The cover 18 here is pivotable in particular about a central axis or the axis of rotation D of the magazine 5. Thus the pivot axis of the cover 18 is in particular coaxial with or identical to the axis of rotation D of the magazine 5.

In the example shown, the cover 18 preferably has a protrusion 19 in the region of the mouthpiece 15 indicated by a broken line for simplification of an intuitive detection of the position of the mouthpiece 15 with the cover 18 closed.

The cover 18 preferably has an annular portion 20 on one or both sides of the inhaler 1 or housing 17. The annular portions 20 in each case preferably engage in corresponding external depressions in the housing 17, so that the cover 18 is pivotable in the required manner and is mounted undetachably on the inhaler 1 or the housing 17 thereof. The cover 18 can preferably be connected to the inhaler 1 or housing 17 by fitting on or latching on.

In the example shown, the cover 18 is in particular at least substantially annular with a broadened or enlarged circumferential region for covering the mouthpiece 15.

In the example shown, the cover 18 covers the inhaler 1 on the side remote from the actuating element 9, if need be also over most and/or all of the surface.

The cover 18 is preferably pivotable from the closed position shown in FIG. 2 by a pivoting movement S into the opened position represented by a broken line. In this opened position, the mouthpiece 15 is freed for the inhalation.

The two positions (closed and open) are preferably delimited in each case by corresponding stops 21 and 22, which are formed by the inhaler 1 or housing 17 or a housing part 24. However, other structural solutions are also possible.

The cover 18 or the annular portion 20 preferably has a central opening at least on a flat side of the inhaler 1, so that the actuating element 9 is accessible.

In the example shown, the actuating element 9 is accessible with the cover 18 both closed and also open.

In the example shown, the actuating element 9 is preferably knob-shaped and/or round or cylindrical.

The inhaler 1 or the housing 17 preferably has a counter for counting the doses or capsules 3 which are already consumed or used or still available for counting or not used. In the example shown, the counter is formed by a corresponding window 23 in the housing 17 and corresponding numbers (not shown) on the magazine 5 or on the capsule chambers 4. However, other structural solutions are also possible.

The inhaler 1 or the housing 17 thereof preferably has a housing part 24 which is coupled undetachably to the rotatable magazine 5 and can be inserted into the housing 17 or attached thereto, in particular in order to close the inhaler 1 or the housing 17 thereof or to form a complete outer housing.

The magazine 5 together with the housing part 24 can be inserted into the inhaler 1. Depending upon the configuration of the inhaler 1, it is also possible that the housing part 24 is replaced together with the magazine 5. In particular, the magazine 5 can only be replaced together with the housing part 24.

Particularly preferably, the housing part 24 and the magazine 5 form a structural unit or assembly which can be easily gripped and handled by a user or patient (not shown).

Figure 3:
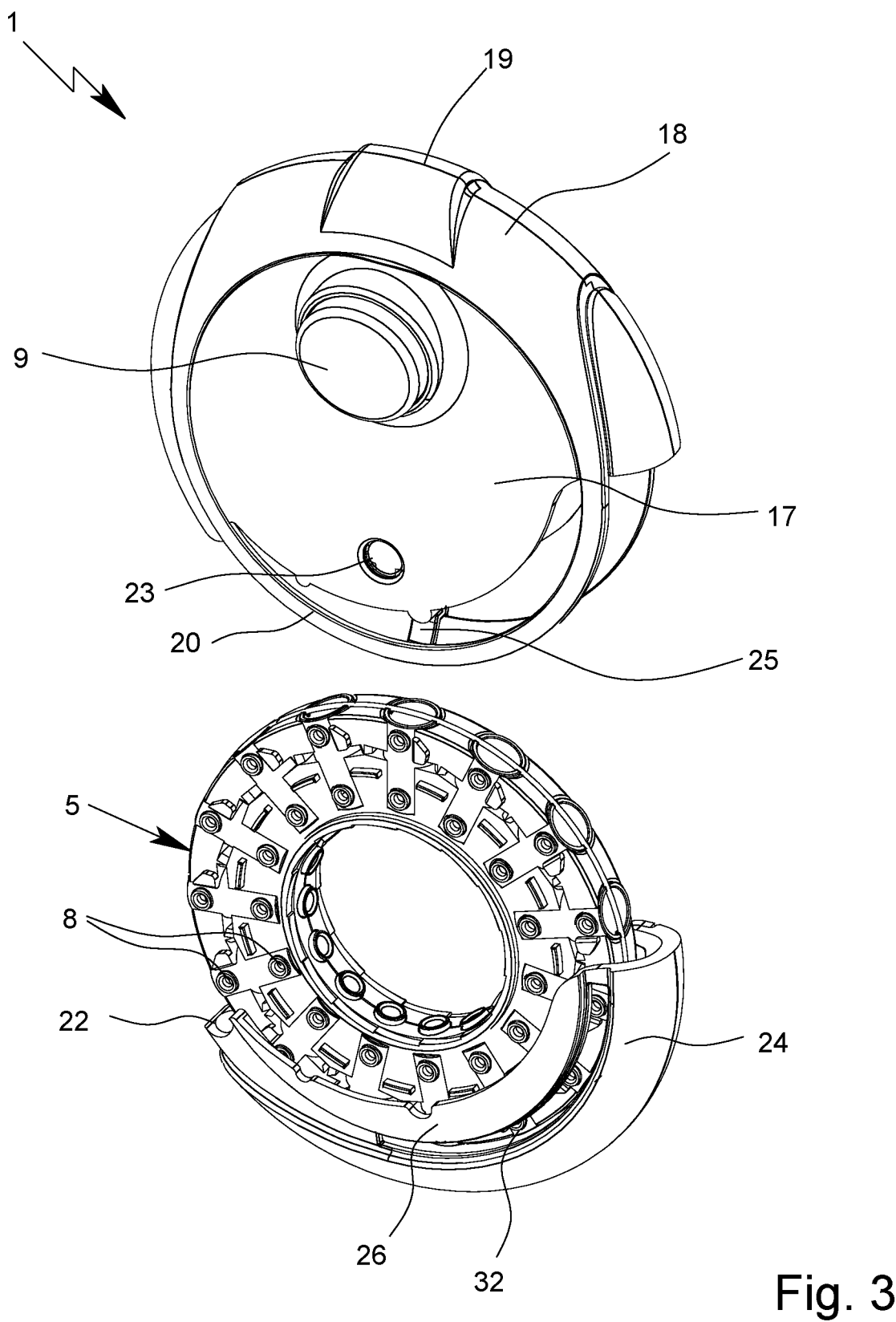
FIG. 3 is an exploded view of the inhaler according to FIG. 2 with separate magazine and housing part.

FIG. 3 shows in a perspective view on the one hand the inhaler 1 and on the other hand the housing part 24 with the associated magazine 5 in the not yet installed state, i.e. in a state moved away from the housing 17.

The housing part 24 can preferably be connected to the inhaler 1 or housing 17 by clamping, by latching and/or undetachably. Where appropriate, the connection or engagement or securing of the housing part 24 on the inhaler 1 or housing 17 can also take place by the engagement of the annular portion 20 and/or a securing portion 25 of the cover 18, as indicated in FIG. 3.

In the example shown, the securing portion 25 engages for example in a depression extending in the circumferential direction and/or behind a corresponding curved portion 26 of the housing part 24, in particular so that the required pivotability of the cover 18 is facilitated or maintained. However, other structural solutions are also possible.

Figure 4:
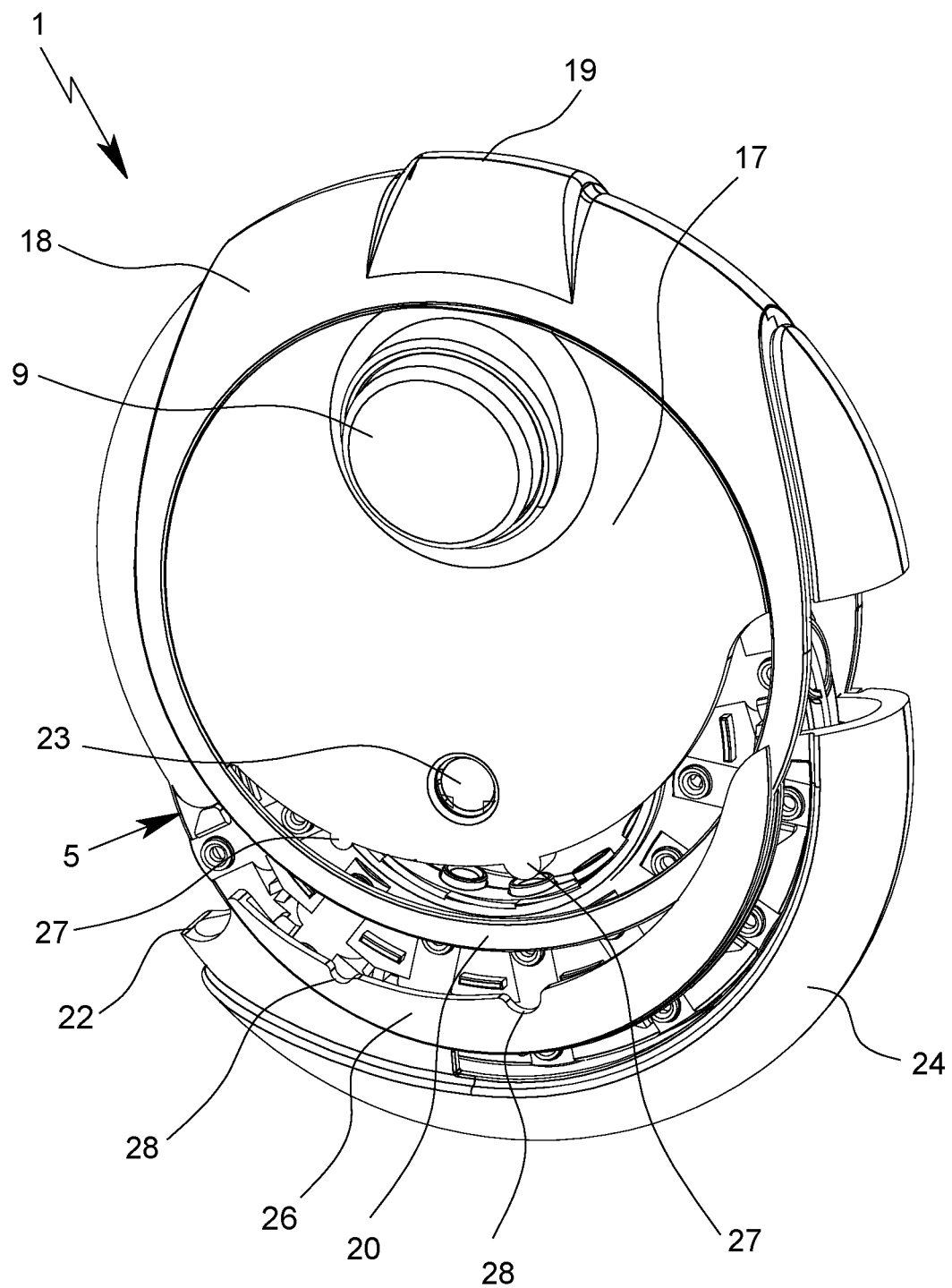
FIG. 4 is a schematic representation of the insertion of the magazine and the housing part into the inhaler.

FIG. 4 shows the inhaler 1, very schematically and only as a detail, just before the complete attachment or insertion of the housing part 24.

The housing part 24 is preferably encoded functionally with respect to the formulation 2 contained in the associated magazine 15. This is preferable in particular when the housing part 24 with the magazine 5 is offered with different formulations 2 for replacement or replenishment or generally together with an inhaler 1, in order to rule out confusion of the formulations 2 and thus to increase the operational safety.

The coding can be achieved for example in that the housing part 24 has at least one first coding element 27, in the example shown two or more coding elements 27, and the inhaler or the housing 17 thereof also has at least one second coding element 28, in the example shown two or more coding elements 28. The coding is obtained for example by the respective shape, size and/or position, in particular in the circumferential direction, of the coding elements 27, 28. In corresponding or contained coding, the first and second coding elements 27, 28 are in particular complementary to one another. For example, they may be projections and indentations or cutouts. The coding may for example also be fixed only by variation of the circumferential position of the coding elements 27, 28. Only in the case of appropriate coding of the first coding elements 27, on the one hand, and the second coding elements 28, on the other hand, can the magazine 5 associated with the housing part 24 be used with the inhaler 1 or be completely inserted therein.

Figure 5:
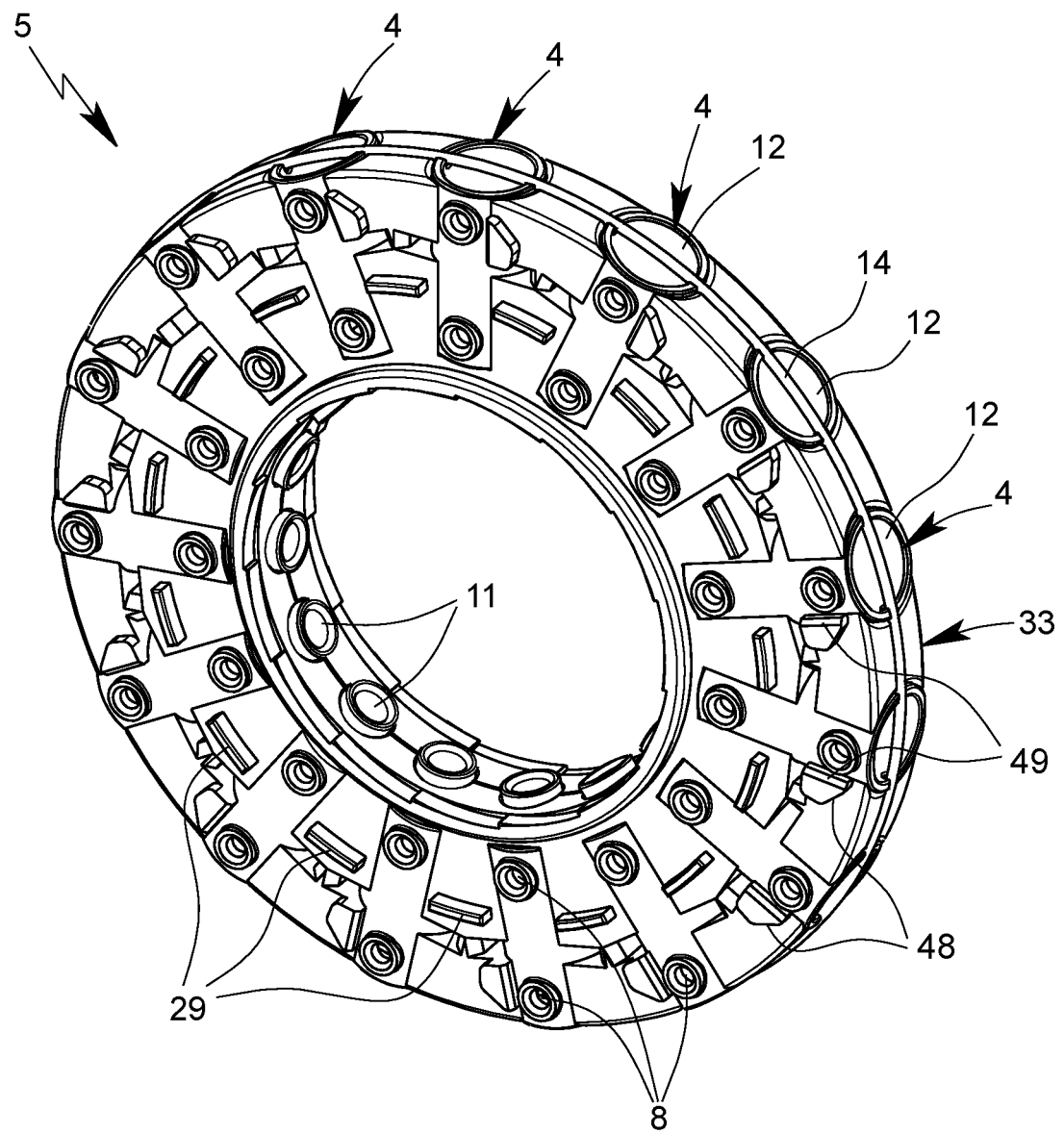
FIG. 5 is a perspective view of the proposed magazine.

FIG. 5 shows the proposed magazine 5 according to a first embodiment which can be used in particular in the inhaler 1 according to the first embodiment. In the perspective view according to FIG. 5, it can be seen that the magazine 5 preferably has axial retaining means, in particular axial projections 29, which are particularly preferably designed as bars or the like extending in the circumferential direction. These serve in particular for the preferably undetachable connection of the magazine 5 to the associated housing part 24.

The magazine 5 is preferably at least substantially annular or annular disc-shaped.

The magazine 5 preferably has a plurality of capsule chambers 4 with capsules 3 received or inserted therein, wherein the capsules 3 cannot be seen in FIG. 5.

The capsules 3 and/or capsule chambers 4 are at least substantially radially oriented with their longitudinal axes.

Figure 6:
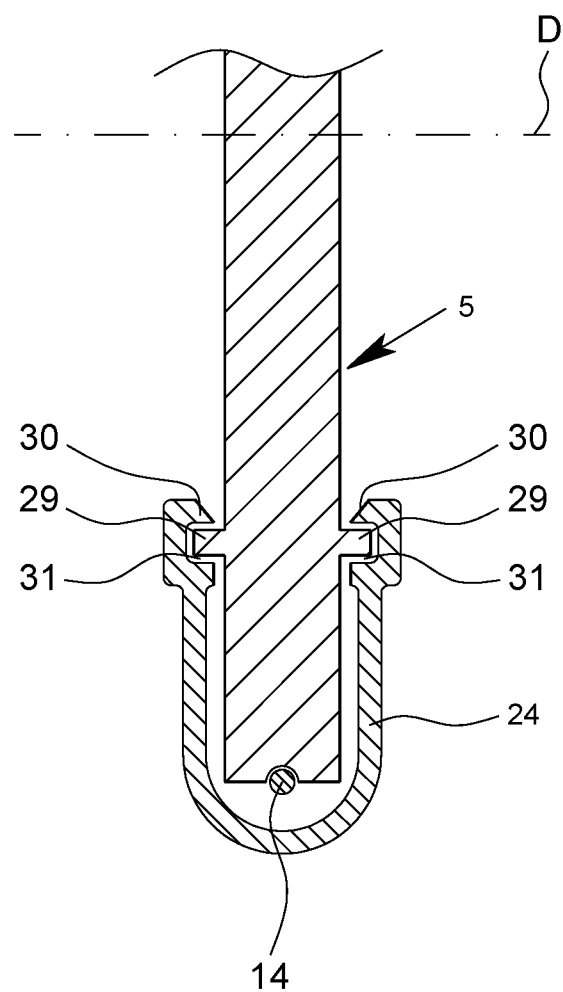
FIG. 6 is a sectional detail of the magazine and housing part in the radial direction.

FIG. 6 shows, in a schematic partial section in the radial direction, how the housing part 24 can be connected to the associated magazine 5 undetachably but rotatably relative to one another. The housing part 24 preferably has retaining portions 30 which engage radially behind the projections 29 preferably formed on both sides of the magazine 5, so that a radial separation of the housing part 24 from the magazine 5 is not possible.

Particularly preferably, the projections 29 can engage or be guided in annular groove portions 31 formed correspondingly on both sides in the housing part 24, in order to achieve a required rotary mounting of the magazine 15. However, this can also be achieved for example in that the magazine 15 with its circumferential surface or its circumferentially arranged securing element 14 is slidably supported on an inner face of the housing part 24. Other structural solutions are also possible.

The retaining portions 30 are preferably in the form of hooks or latching lugs or are provided with a lead-in chamfer or the like, in particular in order to allow the magazine 15 to be radially inserted into the housing part 24 and be connected thereto by latching. However, other structural solutions are also possible.

FIG. 3 indicates that the housing part 24—preferably on opposite sides—preferably has a corresponding depression or opening 32 for in particular axial engagement of the housing 17 or the cover 18, in particular by means of the annular portion 20 or securing portion 25 or the like. However, other structural solutions are possible in particular for latching and/or undetachable or load-bearing connections of the housing part 24 to the inhaler 1 or housing 17.

The inhaler 1 and the magazine 5 are preferably designed in such a way that the magazine 5 can only be inserted in a specific rotational position and/or can be removed or replaced only in a specific rotational position. For example, the magazine 5 can be inserted into the inhaler 1 or the housing 17 thereof only in an initial position, for example with a first capsule chamber 4 adjacent to the mouthpiece 15. The magazine 5 must preferably be completely emptied before it can be removed or replaced again. For this purpose, the magazine 5 can have reached the same position as during insertion or can be located for example in a last or end position.

The magazine 5 preferably has an annular or retaining portion 55 which is designed for example as a circumferential edge and projects axially and for example has at least one or two radial slots at desired rotational positions, as indicated schematically in FIG. 1. The inhaler 1 or the housing 17 thereof preferably has a securing portion 56 which projects axially and engages in the magazine 5 or the edge formed by the retaining portion 55 in such a way that the magazine 5 can be inserted into the inhaler 1 or the housing 17 thereof and/or removed therefrom preferably only in a predetermined rotational position. However, other structural solutions are also possible.

FIG. 5 shows a preferred structure of the magazine 15 according to the first embodiment. This preferably has a support 33 to accommodate the separate or discrete or prefabricated capsule chambers 4.

Figure 7:
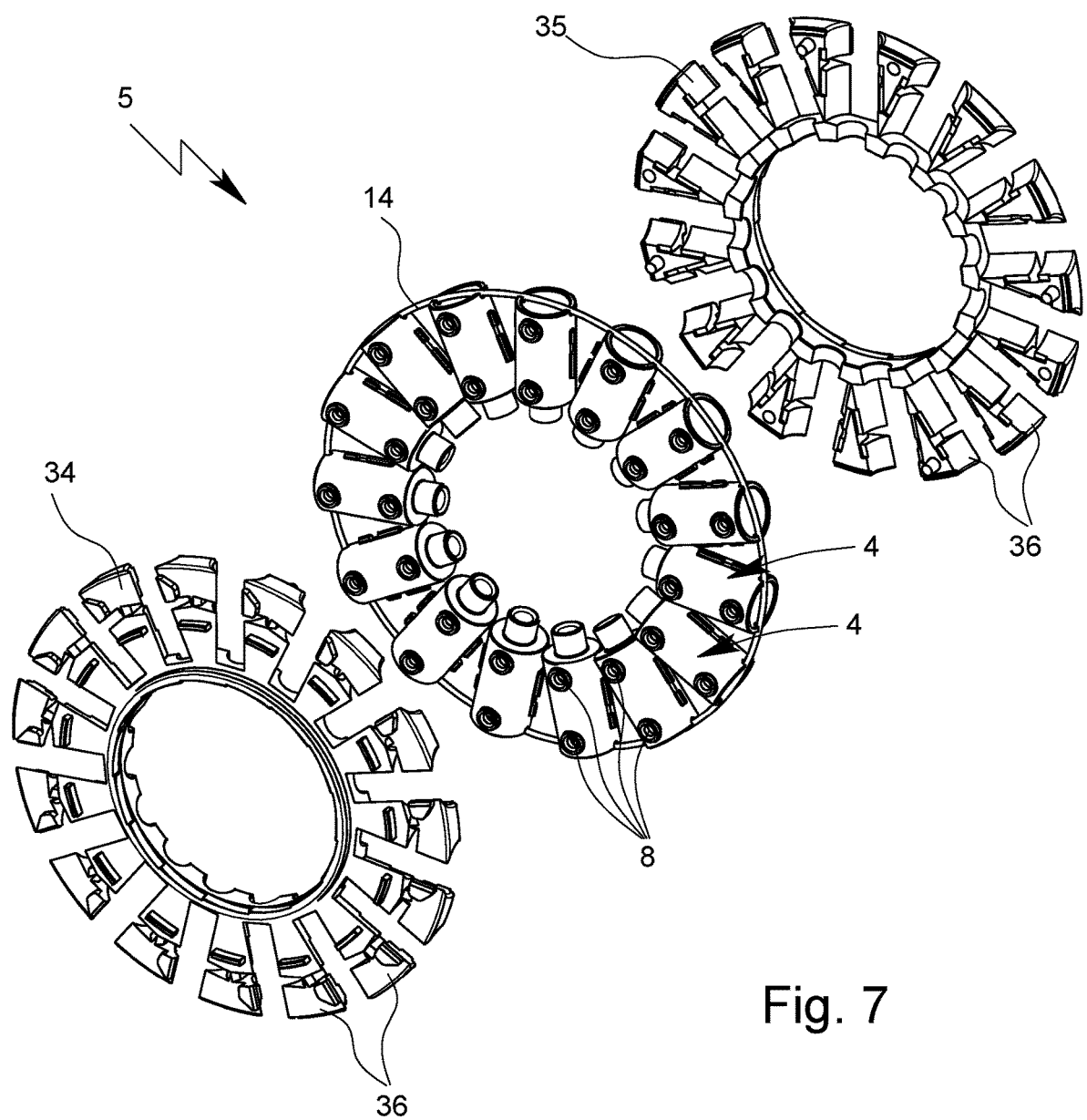
FIG. 7 is an exploded representation of the magazine.

In the example shown, the support 33 is preferably designed in multiple parts and is in particular formed of two support elements 34 and 35, as shown in the exploded view according to FIG. 7. The capsule chambers 4 can be axially inserted or retained between the two support elements 34 and 35. In particular for this purpose, corresponding radial retaining arms 36 are formed by the support 33 or the support elements 34 and 35, which hold the capsule chambers 4 in the assembled state by positive engagement.

The two support elements 34 and 35 can preferably be connected to one another by latching. However, other structural solutions are also possible.

The support 33 is preferably designed in such a way that it fixes or holds the capsule chambers 4 in a defined orientation or rotational position by positive engagement.

The securing element 14 secures the capsule chambers 4 on or in the support 3.

The securing element 14 is preferably annular or in the form of a clamping ring.

The securing element 14 is preferably formed integrally.

The securing element 14 is preferably in the form of wire and/or is preferably made of metal, in particular wire.

Figure 8:
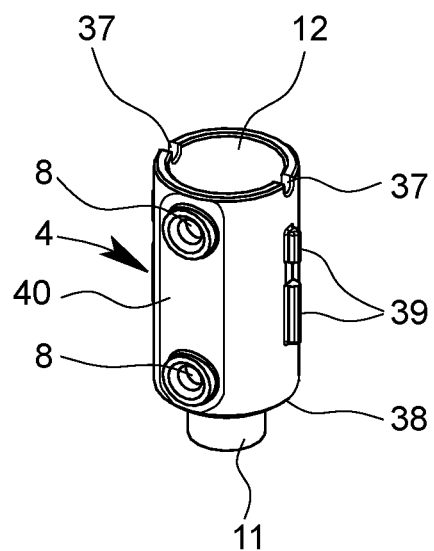
FIG. 8 is a perspective view of a capsule chamber of the magazine.

The capsule chambers 4 are preferably prefabricated or produced as separate parts. FIG. 8 is a schematic perspective view of a preferred configuration of a capsule chamber 4.

The capsule chamber 4 is preferably at least substantially cylindrical. This is advantageous in particular due to the preferably at least substantially cylindrical receiving region for the associated capsule 3 (not shown) in the interior of the capsule chamber 4. However, in principle the capsule chamber 4 can have any other external shape.

The capsule chamber 4 preferably has a possible engagement means, in particular a notch 37, in the example shown two notches 37, in which the securing element 14 can engage. The engagement means or notches 37 serve in particular for axial retention or fixing of the securing element 14. Alternatively or in addition, the engagement means or notches 37 can also serve for fixing the capsule chambers 4 in their rotational position, since in each capsule chamber 4 two notches 37 are shown which are preferably opposite one another.

The engagement means or notches 37 are preferably formed on the outlet side or at the outer axial end, in particular in the axial end face, of the capsule chambers 4. Instead of notches or depressions, the engagement means can also be formed by projections or the like.

The radial position of the capsule chambers 4 can be fixed in particular by radial abutment on the inner end, in particular in the region of the inlet 11 or an outer annular shoulder 38.

Alternatively or in addition, the capsule chambers 4 can in each case also have at least one engagement element 39, in order to be able to fix or hold the capsule chambers 4 in a defined manner and in particular by positive engagement in their rotational position and/or in their radial position in the magazine 5. In the example shown, the engagement element 39 is for example constructed as a projection and/or in the manner of a bar and/or is arranged or formed laterally on the capsule chamber 4. Furthermore, it is also possible that for example two engagement elements 39 are arranged on opposite sides. Other designs and arrangements of the engagement element 39 are also possible.

The piercing or needle openings 8 are preferably already preformed in the capsule chamber 4 or are designed for example as thin-walled opening sites. Thus, if required, the needle openings 8 can be open or openable. Furthermore, it is also possible that the needle openings 8 are self-closing, for example in the manner of a septum, a membrane or the like.

In the example shown, the needle openings 8 are formed in particular by a different material, for example a material which can be pierced or punctured better or is softer or provides better sealing or self-closing than the basic material from which the capsule chamber 4 here is at least substantially produced or made. On the other hand, the basic material is preferably relatively rigid or hard.

In the example shown, the needle openings 8 are preferably formed in each case in a material region 40 made of the different material, as indicated in FIG. 8. In this case, a separate material region 40 can be provided for each needle opening 8 or a common material region 40 can be provided for both needle openings 8 together, as indicated in the example shown.

The material region 40 forming the one or two needle openings 8 is produced from the different material in particular by two-component injection moulding or a similar process.

The piercing of the capsule chambers 4 takes place preferably from a flat face of the magazine 5 or axially or at least substantially axially, i.e. at least substantially parallel to the axis of rotation D of the magazine 5. The needle openings 8 are therefore preferably arranged on a flat face (if required also on opposing flat faces) of the magazine 5 or laterally on the capsule chambers 4.

For use, a user or patient (not shown) opens the inhaler 1 by pivoting or opening the cover 18 in the pivoting direction S (FIG. 2). In this way, the mouthpiece 15 is freed. Furthermore, the opening device 6 is then actuated in particular by pressing of the actuating element 9. As a result, the capsule 3 located in the starting position A, i.e. adjacent to the mouthpiece 15, is opened in its capsule chamber 4 or pierced by means of the needle 7. After release of the actuating element 9, the needles 7 are again retracted and the opened capsule 3 can move freely into its capsule chamber 4.

The inhalation then takes place. The user or patient takes the mouthpiece 15 into the mouth and draws air in. The air is drawn in via the inlet 11 and flows through the capsule chamber 4 or the receiving portion for the capsule 3 and further via the outlet 12 through the mouthpiece 15. This air stream causes the capsule 3 to move to and fro or vibrate or oscillate in particular in the direction of the air stream and thereby assists the discharge of the formulation 2 out of the opened capsule 3 and a fine dispersion of the formulation 2 in the air stream. It should be noted that the dispersion depends upon or is influenced by the vibration path, i.e. in particular by the free movement length of the capsule 3 inside the capsule chamber 4. In the example shown, this distance is delimited in particular by the securing element 14 on the outlet side and by the inner annular shoulder 13 on the inlet side.

After the inhalation, i.e. after the emptying of the capsule 3 located in the discharge position A, the inhaler 1, i.e. the cover 18, can be closed again.

For the next inhalation, it is necessary to move the next capsule 3 (and capsule chamber 4) into the discharge position A, i.e. the position closest to the mouthpiece 15. In the example shown, it is sufficient to further move or rotate the magazine 5 appropriately. There are various possibilities for this.

The movement or pivoting movement of the cover 18 can be used for rotation of the magazine 5. In particular, the opening or closing movement of the cover 18 can be used in order to further rotate the magazine 5 to the next capsule 3 and capsule chamber 4. This can take place for example by means of an entraining pawl, catch or the like on the cover 18, which engages in a suitable manner on the magazine 5 or the support 3 thereof. In this case, it should be borne in mind that the rotation angle of the magazine 5 to the next capsule 3 or capsule chamber 4 can be smaller than the pivoting movement of the cover 18 during opening or closing. Accordingly, only partial coupling of the movements is necessary or expedient. However, in principle it is also possible to adapt the opening or closing of the cover 18, i.e. in particular to provide a pivoting movement different from 90° and a corresponding angular arrangement of the capsules 3 and capsule chambers 4 in the magazine 5, so that in each case with complete entrainment or complete further rotation of the magazine 5 over the entire opening or closing angle of the cover 18 all the capsules 3 and capsule chambers 4 are moved successively into the discharge position A. In this case, the magazine 5 is actually rotated by more than one revolution until it is completely emptied. The capsules 3 are not then emptied in the order of their arrangement in the magazine 5. Accordingly, in the present invention the term "next capsule" should basically be understood to mean that this does not have to be geometrically the next capsule 3 in the magazine 5 (even if this is preferable), but that it may also be the next capsule to be emptied.

Another possibility for further rotating the magazine 5 to the next capsule 3 provides a drive, such as a spring drive, in particular by means of a spring element 52 (indicated schematically in FIG. 2), such as a watch spring or leg spring or the like. In this case, the magazine 5 is rotated by this drive. It is merely necessary to enable further rotation of the magazine 5 to the next capsule 3. This enabling can take place for example by opening or closing the cover 18, for example when reaching a specific position or passing a specific intermediate position, or other actuation, such as actuation of the actuating element 9 of the opening device 6, movement of the mouthpiece 15 or the like.

The spring drive or the spring element 52 can for example be biased so that, for complete emptying of the magazine 5, i.e. for passing through all the required rotational positions, it does not have to be tensioned again. Alternatively, the spring element 52 can also be (additionally) tensioned by the movement of the cover 18, in particular the pivoting for opening and/or closing the cover 18.

Figure 9:
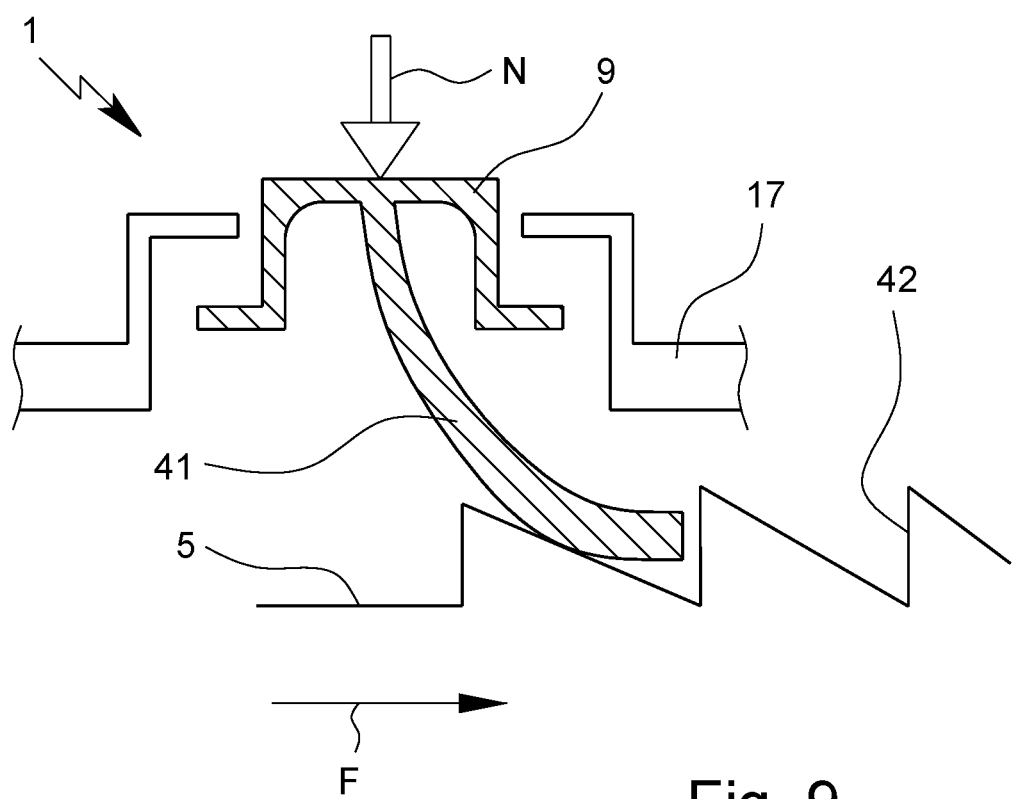
FIG. 9 is a schematic section through the inhaler in the region of an actuating element with a device for driving the magazine.

A further, preferred possibility for driving the magazine 5 or rotating it further consists in converting the movement during the actuation of the actuating element 9 into a corresponding driving movement for the magazine 5. FIG. 9 shows, in a schematic section, a design possibility so that when the actuating element 9 is actuated the magazine 5 is further rotated or cycled to the next capsule 3.

A driving element 41, which is tab-like in particular, is preferably provided and is coupled to the actuating element 9 in particular in such a way that the depressing movement is converted into a rotary movement or transverse movement, i.e. a conveying movement F of the magazine 5. For this purpose, the driving element 41 is preferably designed to be flexible or articulated and engages for example with its free end on a toothing 42 on the magazine 5 or the support 33 thereof, so that when the opening device 6 or the actuating element 9 is actuated again—more precisely in particular before the respective piercing of a capsule 3 located in the discharge position A—first of all a further rotation or cycling of the magazine 5 to the next capsule 3 takes place. However, other structural solutions are also possible here.

The inhaler 1 and the magazine 5 are preferably designed in such a way that the magazine 5 in each case assumes defined rotated positions in which in each case a capsule chamber 4 or capsule 3 is correctly positioned in the discharge position A, in particular so that the connecting portion 16 is connected as tightly as possible to the outlet 12 of the capsule chamber 4 located in the discharge position A and/or so that a certain piercing, in particular precise introduction of the needle 8 into the needle holes 7 is made possible. For this purpose, in particular corresponding engagement means are formed on the magazine 5 or the support 33 thereof, for example by means of the projections 29 which then co-operate with corresponding latching, spring or retaining elements on the housing 17, housing part 24 or another component of the inhaler 1.

Alternatively or in addition, sealing (not shown) is optionally also possible by means of a sealing element or the like between the respective capsule chamber 4 or the outlet 12 thereof, on the one hand, and the adjoining mouthpiece 15 or the connecting portion 16 thereof, on the other hand.

Further preferred embodiments are explained in detail below with reference to the further drawings, wherein in particular only significant differences or new aspects are described in greater detail. The previous statements and explanations are therefore in particular additionally or correspondingly applicable.

Figure 10:
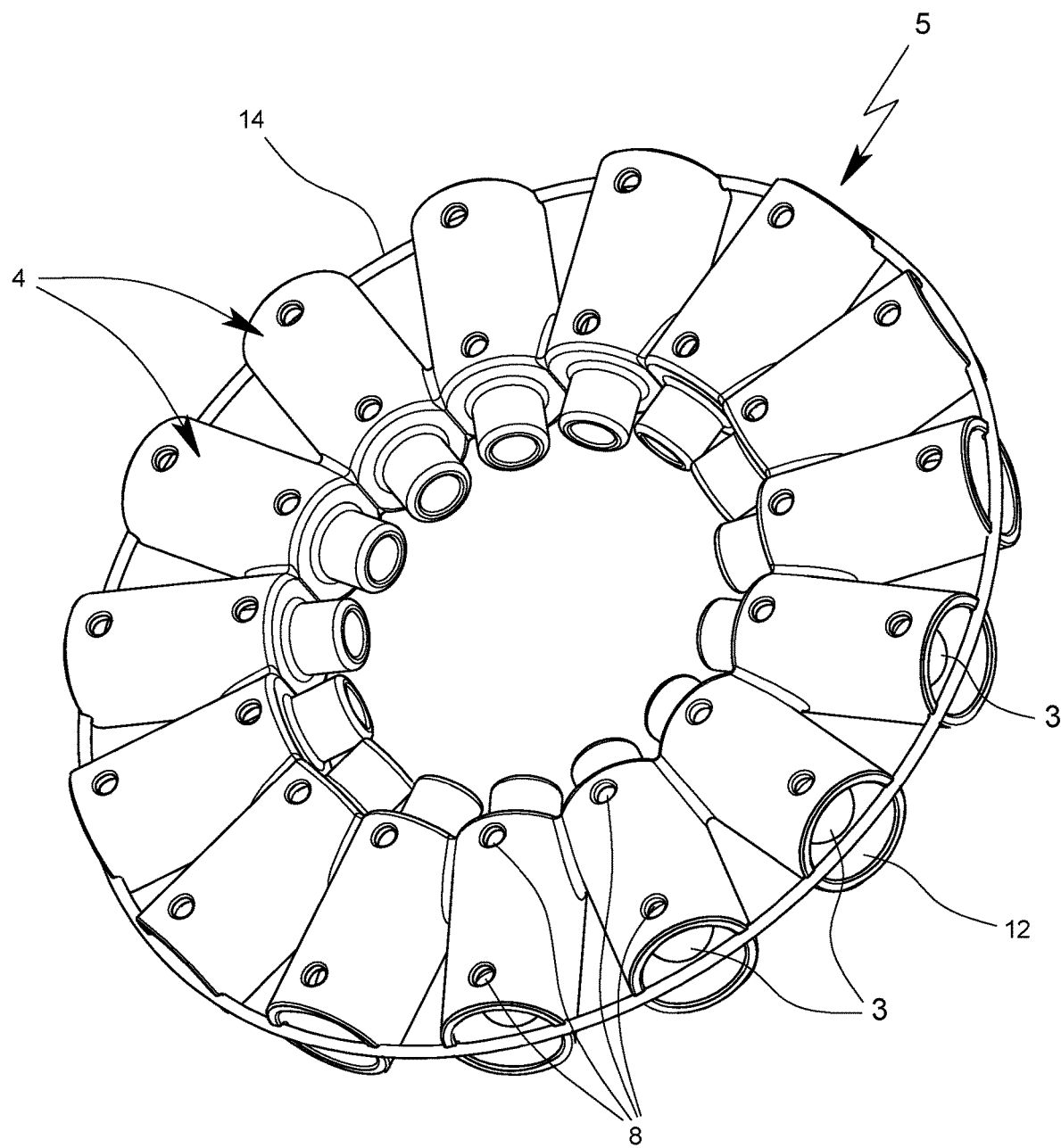
FIG. 10 is a perspective view of a proposed magazine according to a second embodiment.

FIG. 10 is a schematic perspective view of a second embodiment of the proposed magazine 5. The capsule chambers 4 here are all directly connected to one another, and thus in particular form an integral or assembled unit. In particular, a support 33 can be omitted here, or can be provided for stabilisation.

In this embodiment, the capsules 3 are introduced or inserted from the exterior into the capsule chambers 4 and then secured, in this case by the securing element 14.

Alternatively, the magazine 5 or the capsule chambers 4 can also be formed by two shells or halves or the like which are connected to one another.

The capsule chambers 4 are preferably produced here from a rubber-like material, TPE or the like, in particular in such a way that contact points or connections are in particular sealed off without additional means or are at least largely impermeable.

As in the first embodiment, the magazine 5 according to the second embodiment in the example shown preferably comprises 15 capsule chambers 4 and accordingly contains 15 capsules 3. In order to move or cycle the magazine 5 further to the next capsule 3, the magazine 5 must accordingly be rotated by 24° in just the same way as in the first embodiment.

Figure 11:
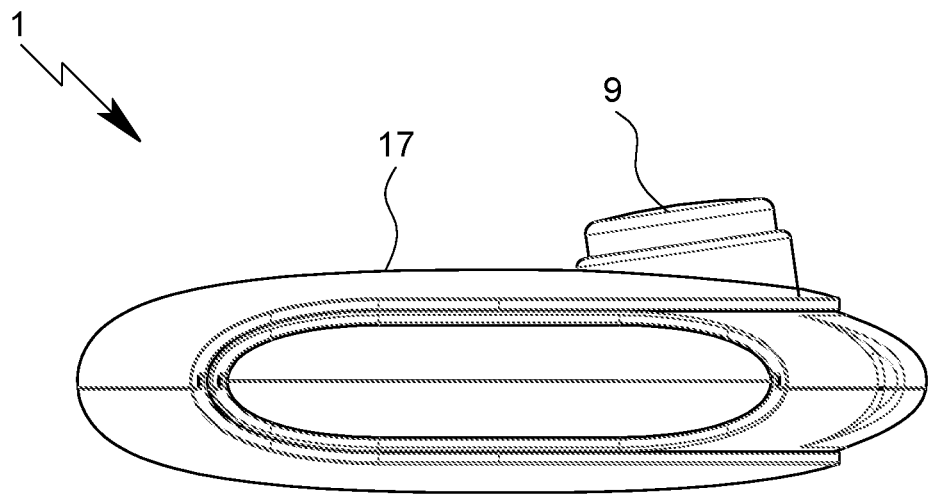
FIG. 11 is a side view of a proposed inhaler according to a second embodiment.
Figure 12:
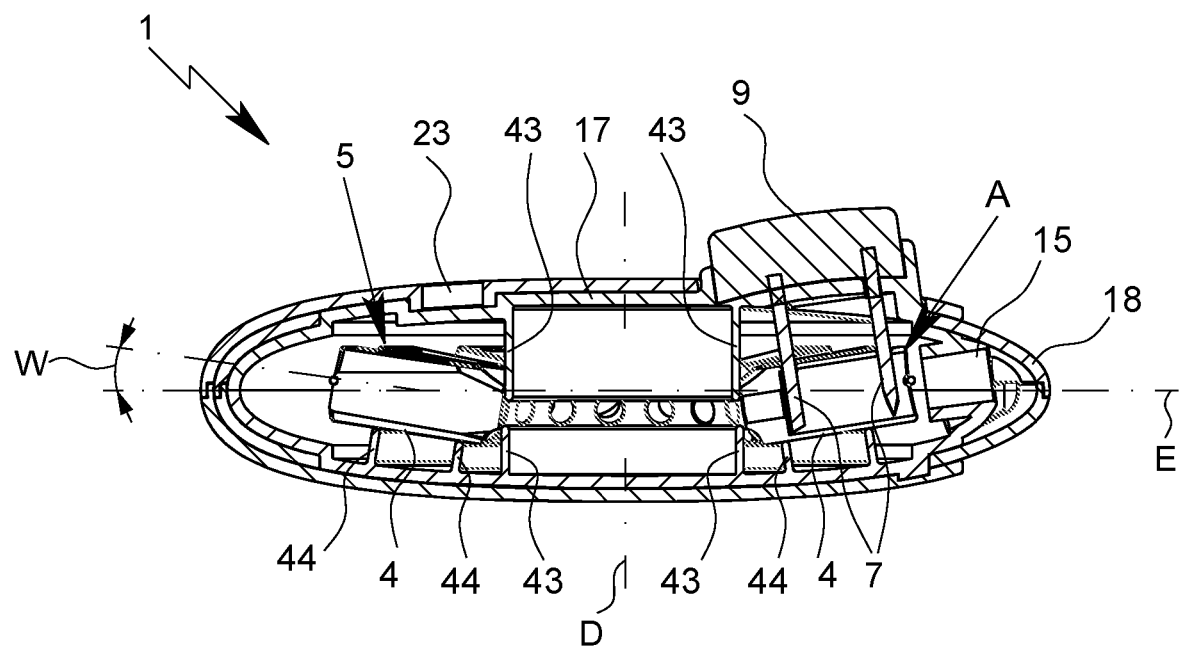
FIG. 12 is a schematic section through the inhaler according to FIG. 11.

FIG. 11 is a side view of a second embodiment of the proposed inhaler 1. FIG. 12 is a schematic section through the inhaler 1, but without capsules 3.

Here the capsule chambers 4 and capsules 3 with their longitudinal axes are basically again oriented at least substantially radially with respect to the disc plane E of the magazine 5 or the flat or disc-like inhaler 1 or with respect to the axis of rotation D of the magazine 5, but somewhat inclined, in particular by an angle W of approximately 5 to 25° and in particular by approximately 10°. This inclination in particular simplifies the filling of the capsule chambers 4 with capsules 3.

The opening device 6 or the needles 7 are preferably inclined accordingly, as indicated in the sectional view according to FIG. 12.

The opening device 6 or the actuating element 9 thereof can also be inclined independently of the preferred inclination of the capsule chambers 4 and capsules 3 by the angle W itself corresponding in particular to the axis of rotation D of the magazine 5 or to the central axis of the inhaler 1.

The aforementioned design is comfortable to operate and makes it easier for or assists a user or patient (not shown) to hold it in the hand, in particular if the inhaler 1 or the housing 17 thereof is designed with a corresponding curve at the rear or is inclined laterally.

A further advantage of this design is that a particularly compact structure or smaller diameter can be achieved, so that the inhaler 1 can in particular be very light and simple to carry in a pocket or the like.

It can be seen from FIG. 12 that the inhaler 1 or the housing 17 thereof preferably has bearing segments 43, 44 for rotatable mounting of the magazine 5 in the inhaler 1. In particular, the bearing segments 43 serve for radial mounting and preferably engage in the centre of the magazine 5 and/or on the capsule chambers 4 in the region of the inner ends or ends on the inlet side.

Alternatively or in addition, the bearing segments 43 preferably engage on one or both axial sides on the magazine 5 or on the capsule chambers 4.

The bearing segments 44 serve in particular for axial mounting and preferably engage axially on the capsule chambers 4 or laterally on the magazine 5.

In particular, an abutment of the magazine 5 or the respective capsule chamber 4 takes place in the region of the discharge position A or on the flat side of the magazine 5 remote from the opening device 6, adjacent to the opening device 6, in order to ensure an abutment of the respective capsule chamber 4 during piercing, in this case by at least one bearing segment 44.

The bearing segments 43 and/or 44 are preferably bar-like, rib-like and/or annular and/or are formed integrally on the housing 17. However, other structural solutions are also possible.

Figure 13:
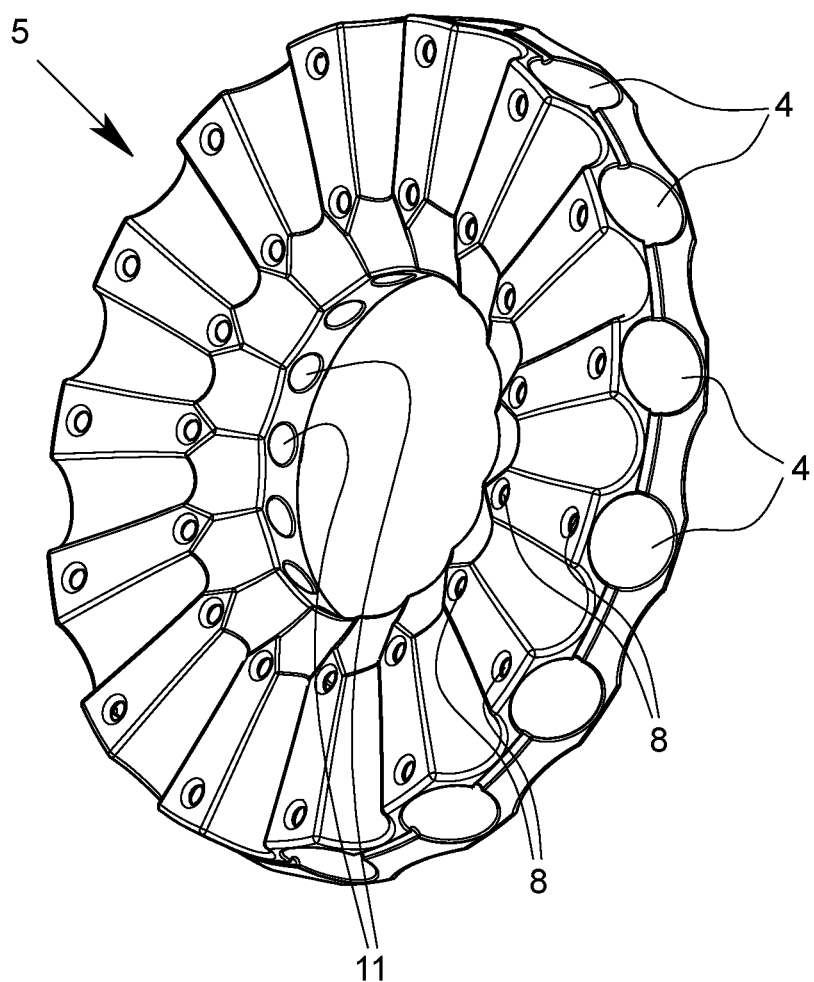
FIG. 13 is a perspective view of a proposed magazine according to a third embodiment.

FIG. 13 is a perspective view of a third embodiment of the proposed magazine 5. This embodiment can be used in particular in the inhaler 1 according to the second embodiment which is shown in FIGS. 11 and 12. The magazine 5 is designed in particular as a relatively soft or flexible ring in which the capsule chambers 4 are formed or in which the capsule chambers 4 can be received or inserted. Particularly preferably, the magazine 5 or the capsule chambers 4 here is/are produced from a resilient or relatively soft and/or rubber-like material. In the illustration according to FIG. 13, the capsules 3 and the securing element 14 are omitted for the sake of simplicity.

Alternatively (not shown), instead of the integral configuration having additional securing elements 14 the magazine 5 can also be made up of two half-shells or halves which fit one another (in particular with a separating plane approximately centrally and longitudinally through the capsule chambers 4), in particular wherein the capsules 4 are inserted into the first half-shell and are covered by the second half-shell.

The half-shells are in this case preferably connected to one another by latching.

The securing elements 14 are preferably moulded onto the half-shells in the form of webs on the openings on the outlet side of the capsule chambers 4.

Due to the preferred use of partially elastic or flexible material for the half-shells, the half-shells abut one another tightly on the long sides of the capsule chambers formed by them, so that no additional air flow occurs through the longitudinal walls of the capsule chambers in the connection region of the half-shells. However, it is also conceivable for additional seals to be inserted in the region of the connection of the two half-shells.

Figure 14:
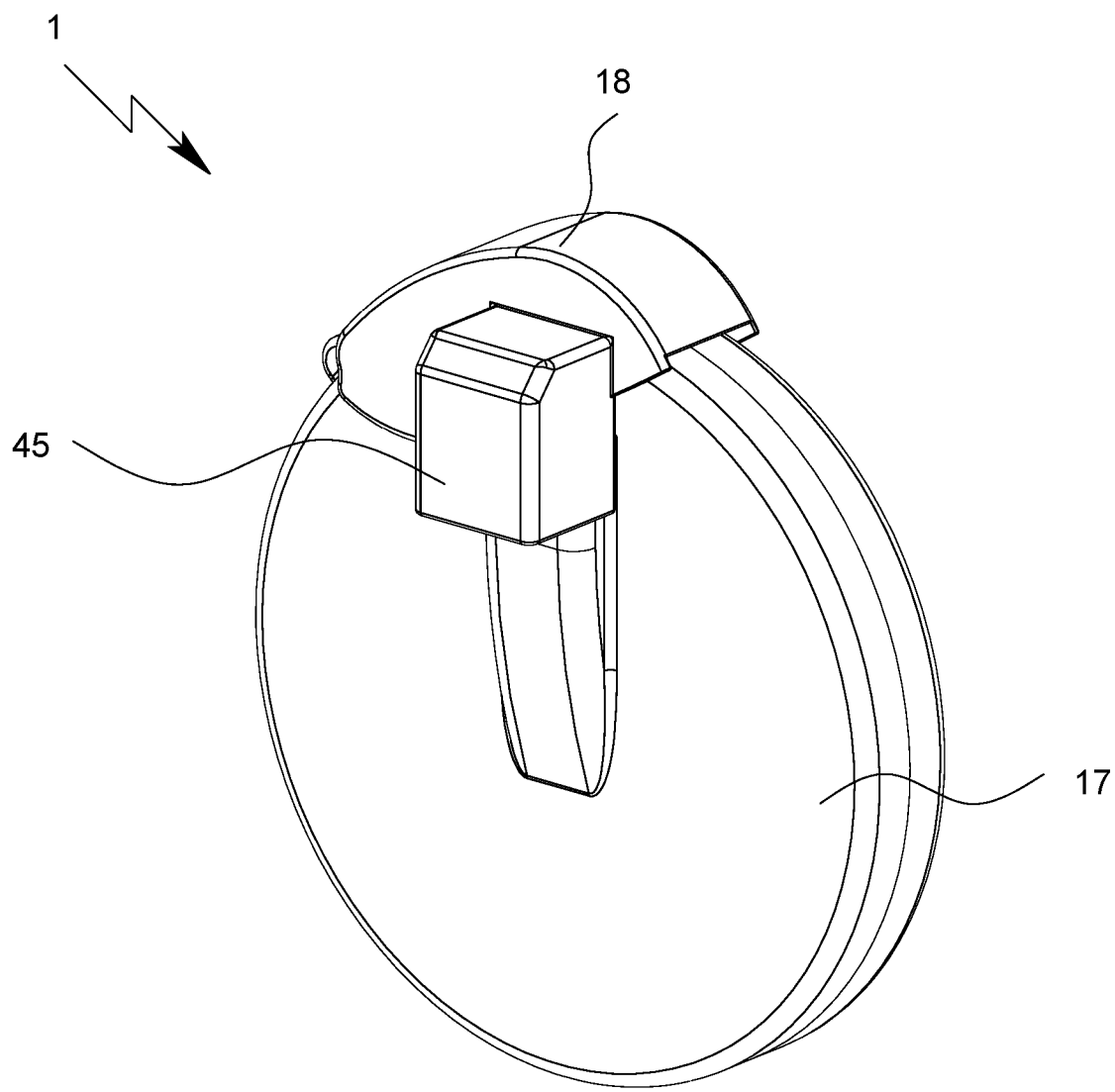
FIG. 14 is a perspective view of a proposed inhaler according to a third embodiment.

FIG. 14 is a perspective view of a third embodiment of the proposed inhaler 1.

In the third embodiment, the cover 18 is preferably articulated peripherally on the inhaler 1 or pivotably mounted externally on the housing 17.

In the third embodiment, the cover 18 preferably has a cover portion 45, which covers the opening device 6 or the actuating element 9 thereof when the cover 18 is closed, so that an actuation of the actuating element 9 is not possible when the cover 18 is closed.

In the drawings relating to this embodiment, the magazine 5 here is preferably designed according to the first magazine embodiment. However, aspects of the other magazine embodiments are also transferable hereto.

Figure 15:
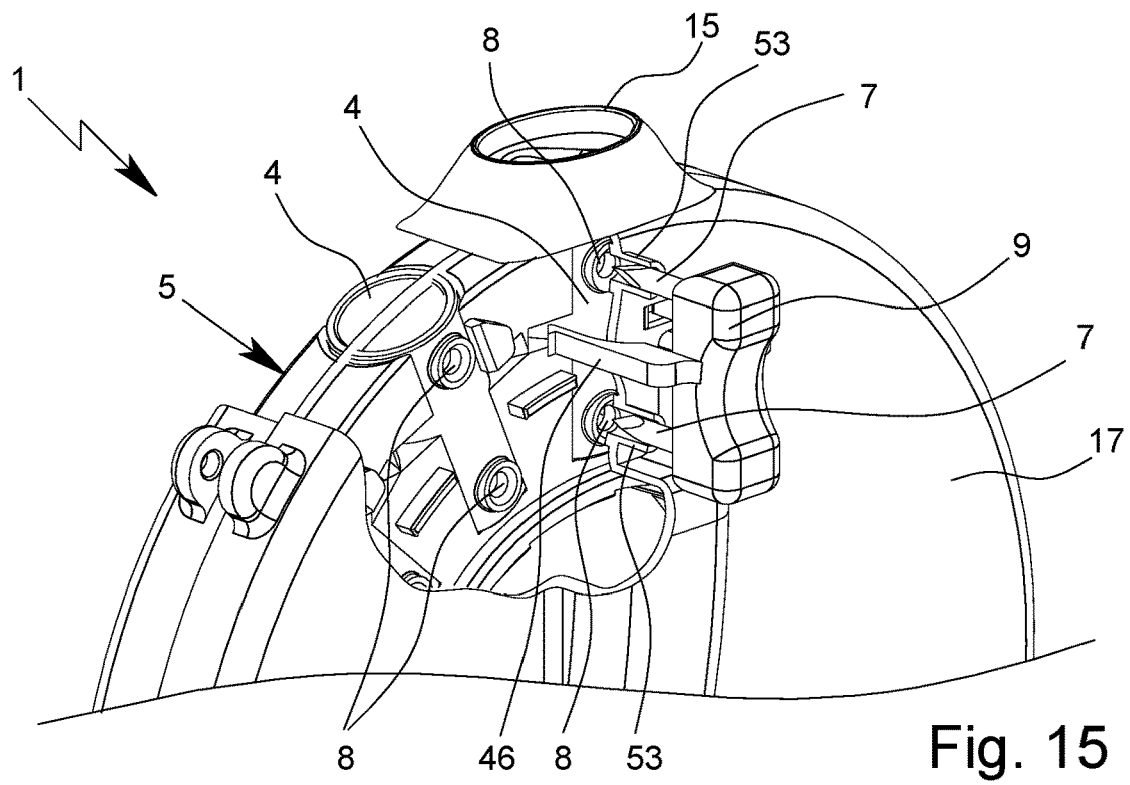
FIG. 15 is another schematic view of the inhaler according to FIG. 14 in the region of a mouthpiece and the opening device.

FIG. 15 shows in a very schematic representation a detail of the inhaler 1 in the region of the mouthpiece 15 and the opening device 6, wherein only a part of the magazine 5 is shown and the housing 17 and the cover 18 are omitted for illustration purposes. The opening device 6 or the actuating element 9 thereof preferably has a guide which, instead of the hollow cylindrical guide sleeve of the housing 17 for the actuating element 9 provided in the first embodiment, now additionally or alternatively has two preferably bar-like guide elements 46, which are guided in the housing 17 or extend through it and which move into the magazine 5 when the actuating element 9 is actuated or pushed in on both sides of the capsule chamber 4 located in the discharge position A, and as a result hold or finely adjust the capsule chamber 4 in the required discharge position A.

In more general terms, in the third embodiment of the inhaler 1 the opening device 6 is preferably provided with an adjusting device in order to move the respective capsule chamber 4 as precisely as possible into the discharge position A and/or to hold it there when the opening or piercing takes place. For this purpose, a corresponding engagement takes place in particular in the magazine 5, preferably in the axial direction, and/or a corresponding engagement takes place on the respective capsule chamber 4, in the example shown preferably by means of the guide elements 46.

Figure 16:
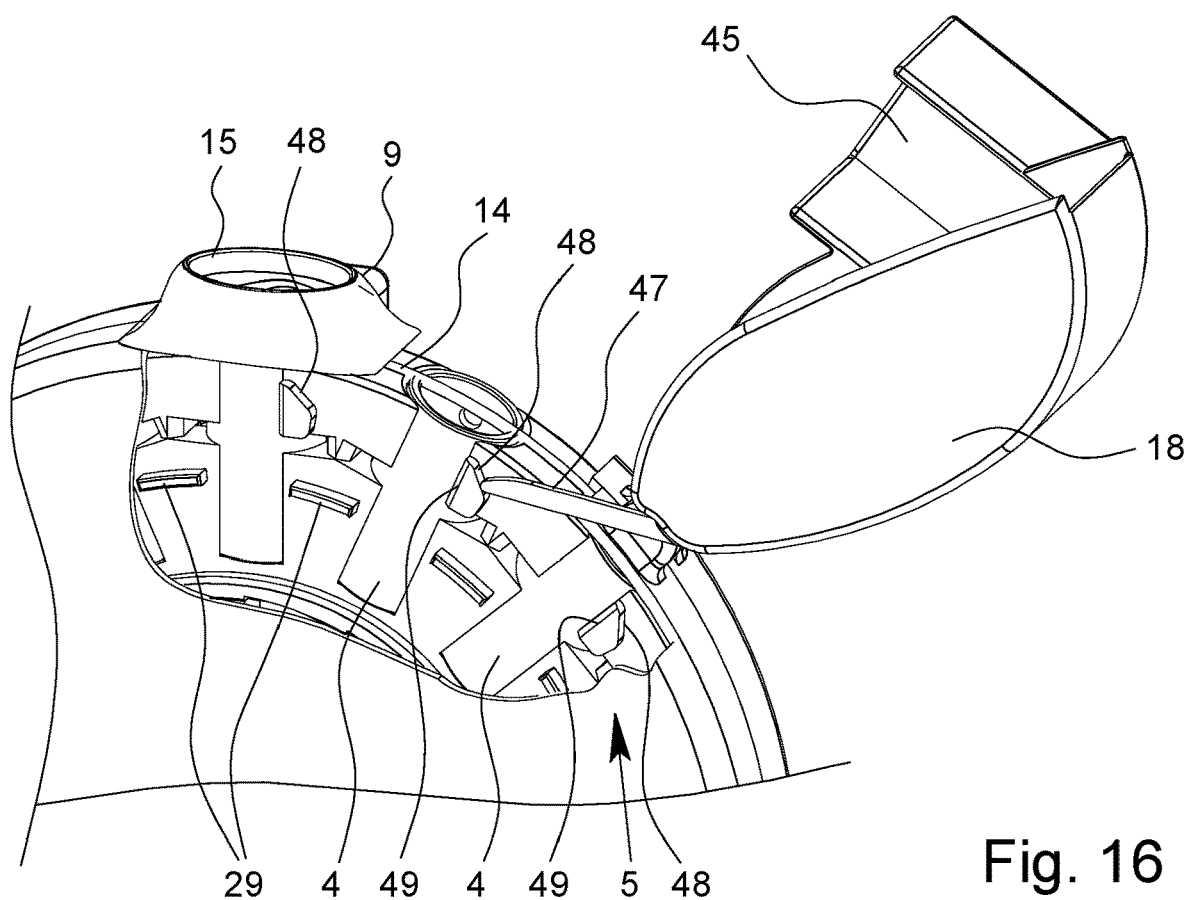
FIG. 16 is a schematic representation of the inhaler according to FIG. 14.

FIG. 16 is a schematic representation of the inhaler 1 in the region of the mouthpiece 15 with the cover 18 opened, wherein the housing 17 is omitted for illustration purposes.

In the third embodiment, the movement of the cover 18 is preferably used for conveying or rotating or cycling of the magazine 5. In particular during opening of the cover 18, the magazine 5 is in each case further rotated to the next capsule 3 or capsule chamber 4.

In the example shown, the inhaler 1 or the cover 18 preferably has a driving element 47, in particular in the form of a spike or finger, which can engage on corresponding engagement portions 48 on the magazine 5 or support 33.

The driving element 47 engages in the interior of the inhaler 1 preferably at least substantially from the circumferential face through a corresponding cutout in the housing 17.

The driving element 47 is preferably resilient, so that it can flex in particular in the axial direction, i.e. parallel to the pivot axis of the cover 18 or parallel to the axis of rotation D of the magazine 5.

The engagement portions 48 preferably form axially projecting shoulders, on which the driving element 47 can engage in each case during opening of the cover 18 for further rotation of the magazine 5 into the next capsule chamber 4. During closing of the cover 18, the driving element 47 is moved back and axially deflected by means of an inclined sliding surface 49, so that it can slide away over the next engagement portion 48 on the magazine 5 in order first of all during the next opening movement of the cover 18 to then move again in the opposite direction and then to engage on this engagement portion 48.

The magazine 15 is preferably secured by means of a backstop, ratchet or the like against turning back, so that during closing of the cover 18 and sliding of the driving element 47 over the respective sliding surface 49 no undesirable turning back of the magazine 5 takes place.

Figure 17:
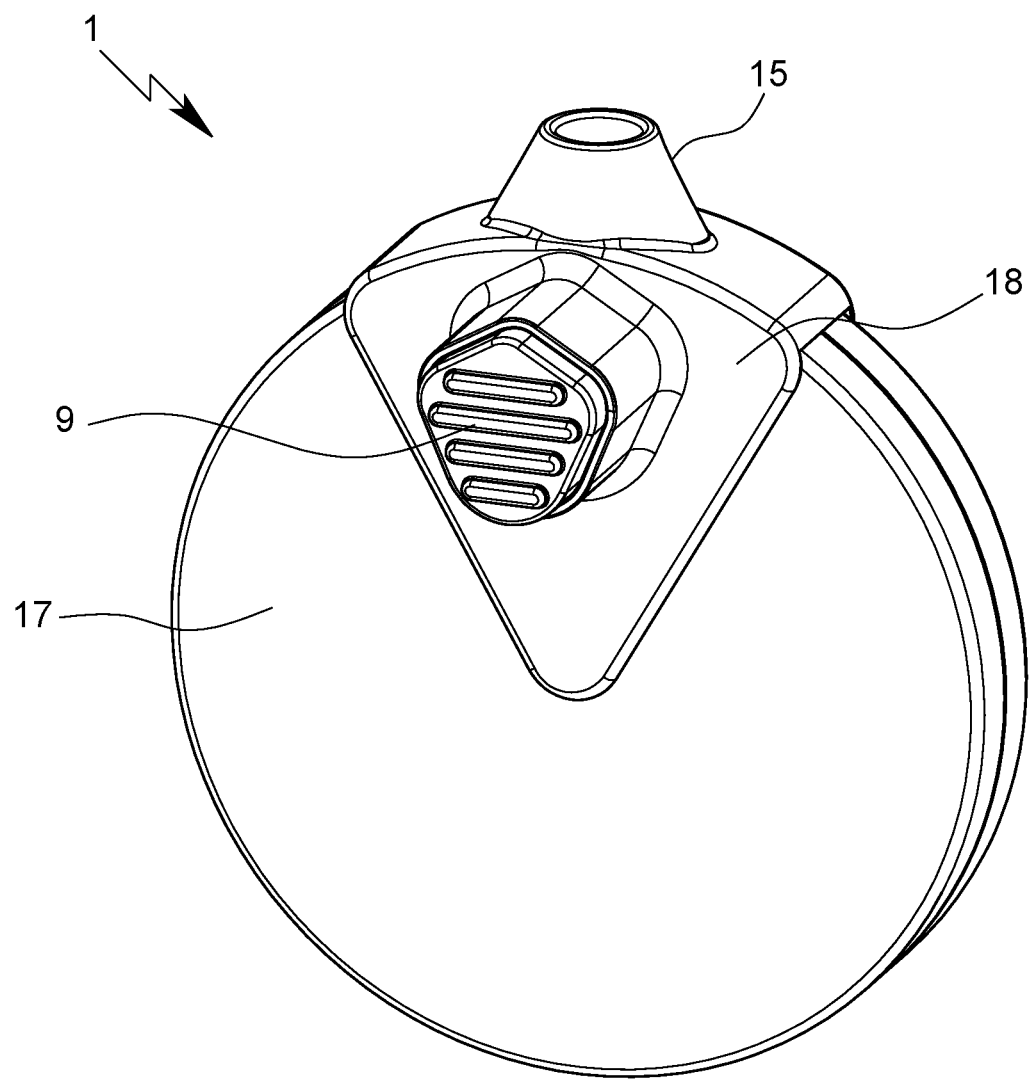
FIG. 17 is a perspective view of a proposed inhaler according to a fourth embodiment.

FIG. 17 is a perspective view of a fourth embodiment of the proposed inhaler 1. Here the opening device 6 and/or the mouthpiece 15, in particular both together, is or are radially movable, preferably in order to achieve thorough sealing of the capsule chamber 4 or needle openings 8 after the opening of a capsule 3 or in order to move or cycle the magazine 5 further to the next capsule chamber 4 or capsule 3. The different functional states and functions are explained in greater detail below with reference to the schematic vertical sections according to FIGS. 18 to 21.

Figure 18:
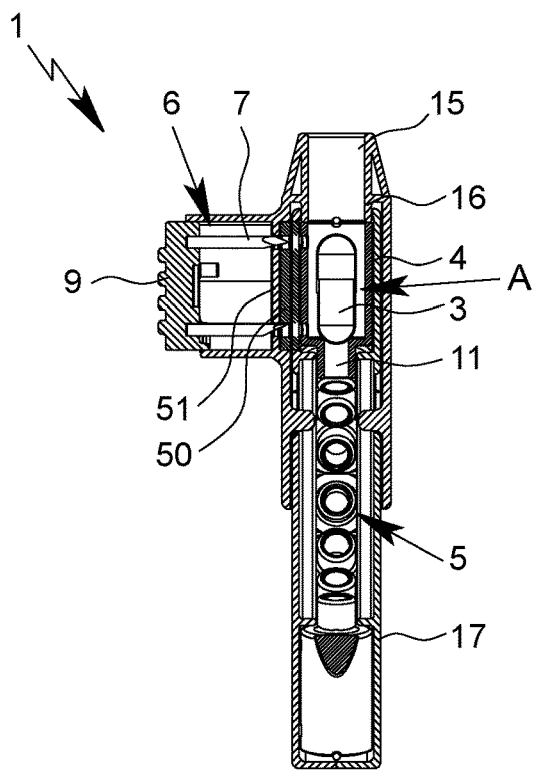
FIG. 18 is a schematic vertical section through the inhaler according to FIG. 17 in a starting position.

FIG. 18 shows the starting position. The capsule 3 is not yet pierced. A capsule chamber 4 with the not yet pierced capsule 3 is located in the discharge position A. The mouthpiece 15 is not pulled out vertically, but is located in its radially inserted position. Thus the mouthpiece 15 or the connecting portion 16 thereof adjoins the capsule chamber 4 or the outlet 12 thereof.

The inhaler 1 preferably has a closure device for closing the needle openings 8, at least during the inhalation. In the example shown, the closure device has or is formed by a sealing element 50 which can be applied externally to the capsule chamber 4.

The sealing element 50 is in particular flat and/or plate-shaped or like a curved channel and/or partially adapted to the external contour of the capsule chamber 4.

The sealing element 50 can be applied from the exterior to the capsule chamber 4, in particular to the respective capsule chamber 4 or successively to the capsule chambers 4.

In particular, a common sealing element 50 is therefore provided for closure of the needle openings 8 of the respective capsule chamber 4 located in the discharge position A during the inhalation.

The sealing element 50 is preferably made of plastics material, in particular TPE (thermoplastic elastomer) or the like.

The sealing element 50 is preferably designed in such a way that it is self-closing and/or self-sealing. Self-closing can be achieved in particular by an appropriate material selection, so that, after puncturing of the sealing element 50 and withdrawal of the needles 7, the openings formed in the sealing element 50 close again autonomously. For this purpose, the sealing element 50 can also be membrane-like or film-like.

The sealing element 50 is in particular associated with the opening device 6 and/or is movable together with the opening device and/or together with the mouthpiece 15 relative to the capsule chamber 4, the magazine 5 and/or the housing 17 and/or in the radial direction.

In the starting position, the sealing element 50 is preferably moved away from the capsule chamber 4 located in the discharge position A, and in particular is received in a depression or cutout 51 in the opening device 6, as indicated in FIG. 18.

Figure 19:
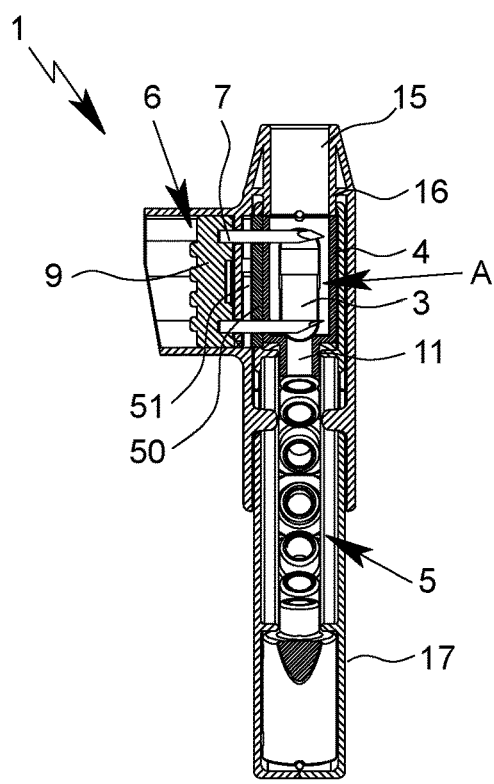
FIG. 19 is a schematic vertical section through the inhaler according to FIG. 17 in the actuated piercing position.

FIG. 19 shows the state after the actuation. The actuating element 9 has been pressed in. The needles 7 have been moved forwards towards the capsule chamber 4. In this case, the needles 7 initially entrain the sealing element 50 and bring it outside for abutment on the capsule chamber 4. Furthermore, the needles 7 puncture or penetrate the sealing element 50 (completely) and are moved in through the needle holes 8 into the capsule chamber 4, so that finally the capsule 3 located therein is pierced, as indicated in FIG. 19.

Figure 20:
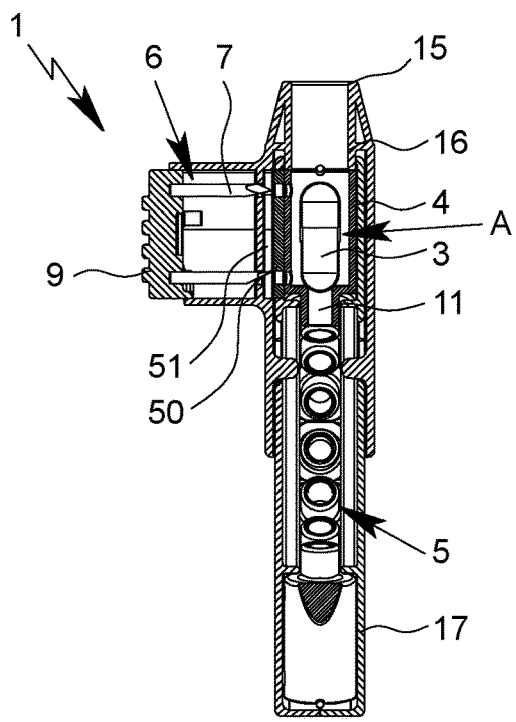
FIG. 20 is a schematic vertical section through the inhaler according to FIG. 17 after actuation of the piercing device.

After the opening or piercing of the capsule 3, the actuating element 9 is released again. The actuating element 9 and the needles 7 retract automatically, in particular due to the spring(s) 10 (not shown in FIGS. 18-21 for the sake of simplicity, but preferably present in operation as in FIG. 1), but the sealing element 50 remains in its sealing position and/or its position bearing on the capsule chamber 4. This state is indicated in FIG. 20. In this state, the sealing element 50 at least substantially seals the needle holes 8 in order to avoid or at least to minimise an undesirable inflow of air through the needle holes 8 during inhalation.

The sealing element 50 is preferably self-adhesive and/or a material pairing is selected for the capsule chamber 4 or the outer face thereof in the region of the needle openings 8, on the one hand, and for the sealing element 50, on the other hand, such that a relatively high adhesion is achieved in order to ensure that, even when the needles 7 retract, the sealing element 50 adheres to or remains on the capsule chamber 4, in order to at least substantially close or cover the needle openings 8.

Alternatively, the sealing element 50 can also have associated with it a guide along which the sealing element 50 can be displaced by a small lever, for example on the actuating element 9. In this case, the sealing element 50 can likewise have openings which, due to a displacement of the sealing element 50 during actuation of the actuating element 9, in particular during pressing of the actuating element 9, become congruent with the needle openings 8 of the respective capsule chamber 4 so that, with the actuating element 9 pressed, the needles 7 project both through the sealing element 50 and also through the wall of the capsule chamber 4 into the openings in each case provided for this purpose. If the needles 7 are retracted or the actuating element 9 moves back, the sealing element 50 is preferably displaced by means of the guide and/or the lever or the like, in particular so that the openings of the sealing element 50 are no longer congruent with the needle openings 8 in the capsule chamber 4 or the sealing element 50 seals or covers the needle openings 8 in the capsule chamber 4.

The inhaler 1 is now ready for inhalation. When the inhalation has taken place, the mouthpiece 15 together with the actuating device 9 is moved or pulled radially outwards. This is done manually by a user or patient (not shown).

Figure 21:
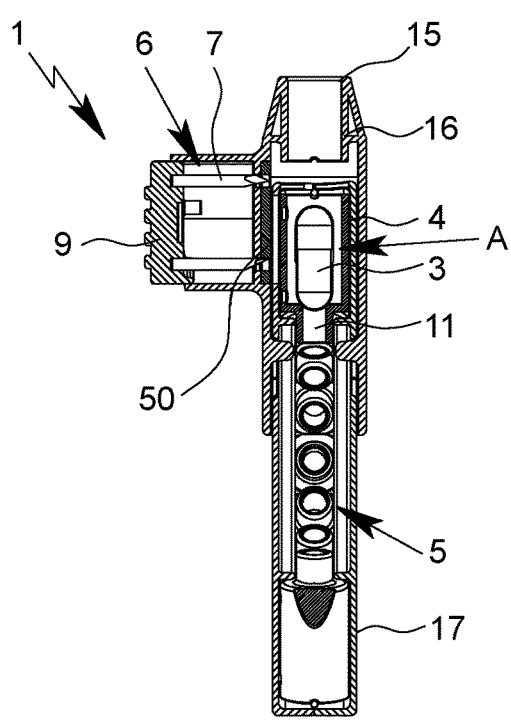
FIG. 21 is a schematic vertical section through the inhaler according to FIG. 17 with the mouthpiece raised or moved away.

FIG. 21 shows the corresponding state when the mouthpiece 15 has radially moved away or moved outwards.

During the radial movement or relative movement, the sealing element 50 is entrained and thereby released from the capsule chamber 4. Thus the sealing element 50 is (also) moved relative to the capsule chamber 4, in particular in the direction of the contact surface and/or in the direction of the longitudinal axis of the capsule chamber 4. In the moved-away state, the sealing element 50 is preferably received again in the cutout 51, as indicated in FIG. 21.

Lastly, the mouthpiece 15 is again radially pushed in or moved back. Due to this movement, the magazine 5 is preferably moved further or rotated further, so that the next capsule chamber 4 is moved into the discharge position A. This further movement or further rotation can take place due to a corresponding (operational) coupling of the radial movement to the rotary movement or for conversion into a rotary movement of the magazine 5. Alternatively, for example a release can also be effected by the radial movement, so that the magazine 5 can be further rotated to the next capsule chamber 4, for example by means of the spring element 52 or the like. In this last-mentioned case, the magazine 5 is not driven by the radial movement or relative movement of the mouthpiece 15, but by the leg spring or another drive.

When the mouthpiece 15 has again been pushed in radially, the starting position according to FIG. 18 is again assumed. Furthermore, the magazine 5 has then been moved further or rotated further; i.e. a new capsule chamber 4 with a still unopened capsule 3 is located in the discharge position A. Thus the inhaler 1 is ready for opening or piercing the capsule 3.

The different embodiments of the inhaler 1 and individual features and aspects of the different embodiments can be combined with one another in any way, but can also be implemented independently. The same applies to the magazine 5 and to the use of the different embodiments of the magazine 5 in different inhalers 1.

In the inhalers 1 and magazines 5 or capsules 3 described here, medical formulations are preferably used which have a constituent as set out in particular in WO 2009/115200 A1, preferably on pages 25 to 40, or in EP 2 614 848 A1, preferably on page 26, line 21, to page 63, line 2, or have formulations corresponding thereto. The content of those lines is hereby incorporated in full, including features, into the present application.

List of reference signs:

| | |
|---|---|
| 1 | inhaler |
| 2 | formulation |
| 3 | capsule |
| 4 | capsule chamber |
| 5 | magazine |
| 6 | opening device |
| 7 | needle |
| 8 | needle opening |
| 9 | actuating element |
| 10 | spring |
| 11 | inlet |
| 12 | outlet |
| 13 | inner annular shoulder |
| 14 | securing element |
| 15 | mouthpiece |
| 16 | connecting portion |
| 17 | housing |
| 18 | cover |
| 19 | protrusion |
| 20 | annular portion |
| 40 | material region |
| 41 | driving element |
| 42 | toothing |
| 43 | bearing segment (radial) |
| 44 | bearing segment (radial) |
| 45 | retaining portion |
| 46 | guide element |
| 47 | driving element |
| 48 | engagement portion |
| 49 | sliding surface |
| 21 | stop |
| 22 | stop |
| 23 | window |
| 24 | housing part |
| 25 | securing portion |
| 26 | curved portion |
| 27 | first coding element (housing) |
| 28 | second coding element (housing part) |
| 29 | projection |
| 30 | retaining portion |
| 31 | annular groove portion |
| 32 | depression/opening |
| 33 | support |
| 34 | support element |
| 35 | support element |
| 36 | retaining arm |
| 37 | notch |
| 38 | outer annular shoulder |
| 39 | engagement element |
| D | axis of rotation |
| E | plane |
| H | main discharge direction |
| S | pivoting movement |
| N | depressing movement |
| F | conveying movement |
| W | angle |

-continued

List of reference signs:

| | |
|---|---|
| 50 | sealing element |
| 51 | cutout |
| 52 | spring element |
| 53 | needle guide |
| 54 | needle guide |
| 55 | retaining portion |
| 56 | securing portion |
| A | discharge position |
| B | movement |

The invention claimed is:

1. An inhaler (1) for inhalation of a formulation (2) in powder form, comprising:
   a magazine (5) which is rotatable and contains pre-dosed doses of the formulation (2) in capsules (3),
   a housing (17) which is substantially flat or disc-shaped within a main plane (E), the housing (17) having a housing part (24) in which the rotatable magazine (5) is disposed, and
   capsule chambers (4) within the magazine (5), each containing a respective one of the capsules (3),
   wherein at least one of the capsules (3) and the capsule chambers (4) are secured in the magazine (5) by a single securing element (14) in such a way that dispensing respective doses of the formulation (2) from the respective capsules (3) is carried out without removal of the securing element (14) from the capsule chambers (4),
   wherein the securing element (14) is in the form of an annularly extending element, including at least one of a wire and clamping ring,
   wherein the housing part (24) is fixedly coupled to the rotatable magazine (5), and is removable from the housing (17) in order to facilitate replacement of the magazine (5) by inserting a new magazine, and
   the housing part (24) and the magazine (5) are inserted into the housing (17) of the inhaler (1) in a direction, which is parallel to a main plane (E) of the magazine (5) and the housing (17).

2. The inhaler according to claim 1, wherein the housing part (24) forms a circumferential portion along the magazine (5) and/or housing (17).

3. The inhaler according to claim 1, wherein the direction is a radial direction of the main plane (E) of the magazine (5) and the housing (17).

4. The inhaler according to claim 1, the housing part (24) has a first coding element (27) and the housing (17) has a second coding element (28), wherein the first and second coding elements (27, 28) only engage in one another when a coding thereof matches, so that the magazine (5) and the housing part (24) can only be inserted into the housing (17) of the inhaler (1) when the coding matches.

5. The inhaler according to claim 1, further comprising:
   a mouthpiece operable to deliver the formulation (2) to a user when dispensed;
   a cover (18) for the mouthpiece (15), the cover (18) being coupled to the magazine (5) in such a way that at least one of:
   a pivoting of the cover (18) operates to open and close the mouthpiece (15) and operates to rotationally index the magazine (5) for a next dose, and the cover (18) is pivotable for opening and closing of the mouthpiece, where pivoting the cover (18) biases a spring element (52) for further movement of the magazine (5).

6. The inhaler according to claim 1, further comprising:

capsule chambers (4) within the magazine (5), each containing a respective one of the capsules (3), and each including at least one needle opening (8), an opening device (6) having at least one needle (7) for piercing the respective capsules (3) within the respective capsule chambers (4) through the at least one needle opening (8), and a closing device for closing the at least one needle opening (8) of a given one of the capsule chambers (4) during the inhalation of formulation (2) from the respective capsule (3) within such given one of the capsule chambers (4), wherein the closing device comprises a sealing element (50) which is applied externally to the given one of the capsule chambers (4) for closing the at least one needle opening (8) thereof during the inhalation of the formulation (2).

7. The inhaler according to claim 6, wherein at least one of:

the sealing element (50) is flat or plate-shaped, the sealing element (50) has an opening for freeing the at least one needle opening (8), the sealing element (50) is movable or displaceable, with at least one of the opening device (6) and a mouthpiece (15) of the inhaler (1), transversely with respect to the at least one needle opening (8), the sealing element (50) is applied automatically to the capsule chamber (4) or the at least one needle opening (8) from an exterior during inhalation, and the sealing element (50) is resiliently biased against the capsule chamber (4) or the at least one needle opening (8) from the exterior.

8. The inhaler according to claim 1, wherein:

the capsule chambers (4) are arranged in a prefabricated, annular manner, into the magazine (5), and the capsules (3) are elongated and are oriented with respective longitudinal axes thereof obliquely oriented with respect to an axis of rotation (D) of the magazine (5).

9. A magazine (5) for an inhaler (1) for inhalation of a formulation (2) in powder form, comprising:

capsule chambers (4) within the magazine (5), each containing a respective one of the capsules (3), and each one of the capsules (3) containing a dose of the formulation (2), wherein:

the capsule chambers (4) are arranged in a prefabricated, annular manner, into the magazine (5), at least one of the capsules (3) and the capsule chambers (4) are secured in the magazine (5) by a single securing element (14) in such a way that dispensing respective doses of the formulation (2) from the respective capsules (3) is carried out without removal of the securing element (14) from the capsule chambers (4), the securing element (14) is in the form of an annularly extending element, including at least one of a wire and clamping ring, and the capsules (3) are elongated and are oriented with respective longitudinal axes thereof obliquely oriented with respect to an axis of rotation (D) of the magazine (5).

10. The magazine according to claim 9, wherein the magazine (5) has an integral or multi-part support (33) to accommodate the capsule chambers (4).

11. The magazine according to claim 10, wherein the support (33) is flexible or rubber-elastic.

12. The magazine according to claim 10, wherein the support (33) is substantially rigid.

13. The magazine according to claim 9, wherein the securing element (14) is arranged on an outer circumference of the magazine (5).

14. The magazine according to claim 9, wherein the capsules (3) and/or capsule chambers (4) are oriented substantially radially.

15. The magazine according to claim 9, wherein piercing or needle openings (8) are pre-formed in the capsule chambers (4) or are configured as walled opening sites that are pierceable.

16. The magazine according to claim 9, wherein the capsule chambers (4) have needle openings (8) which are self-closing.

* * * * *